US012663355B2

(12) United States Patent
Hu et al.

(10) Patent No.: US 12,663,355 B2
(45) Date of Patent: Jun. 23, 2026

(54) DISPLACEMENT DEVICES

(71) Applicant: SOUTHWEST PETROLEUM UNIVERSITY, Chengdu (CN)

(72) Inventors: Yisheng Hu, Chengdu (CN); Lei Pu, Chengdu (CN); Jin Wang, Chengdu (CN); Chenhui Shi, Chengdu (CN)

(73) Assignee: SOUTHWEST PETROLEUM UNIVERSITY, Chengdu (CN)

( * ) Notice: Subject to any disclaimer, the term of this patent is extended or adjusted under 35 U.S.C. 154(b) by 309 days.

(21) Appl. No.: 18/632,242

(22) Filed: Apr. 10, 2024

(65) Prior Publication Data

US 2024/0337579 A1     Oct. 10, 2024

(30) Foreign Application Priority Data

Apr. 10, 2023    (CN) .......................... 202310370523.4

(51) Int. Cl.
| | |
|---|---|
| *G01N 15/00* | (2024.01) |
| *G01N 15/08* | (2006.01) |
| *G01N 29/024* | (2006.01) |
| *G01N 29/14* | (2006.01) |
| *G01N 33/24* | (2006.01) |

(52) U.S. Cl.
CPC ..... *G01N 15/0826* (2013.01); *G01N 15/0806* (2013.01); *G01N 29/024* (2013.01); *G01N 29/14* (2013.01); *G01N 33/24* (2013.01)

(58) Field of Classification Search
CPC ........... G01N 15/0826; G01N 15/0806; G01N 29/024; G01N 29/14; G01N 33/24
See application file for complete search history.

(56) References Cited

U.S. PATENT DOCUMENTS

2022/0290561 A1*    9/2022   Guo ...................... E21B 49/088

FOREIGN PATENT DOCUMENTS

| | | | | |
|---|---|---|---|---|
| CN | 201555791 U | * | 8/2010 | |
| CN | 112255253 A | * | 1/2021 | ........... G01N 23/046 |
| CN | 116337719 A | * | 6/2023 | ......... G01N 15/0806 |

* cited by examiner

*Primary Examiner* — Jamel E Williams
(74) *Attorney, Agent, or Firm* — PORUS IP LLC

(57) ABSTRACT

Embodiments of the present disclosure provide a displacement device, comprising a plate model, a cylinder, a circulation component, a confining pressure pump, a displacement component, an acoustic detection component, and a pipeline component. The plate model includes a model cavity and a rock plate disposed in the model cavity, and the rock plate is provided with a sealing member on a surface. The sealing member is provided with an electrode sheet, and acoustic waves generated by the acoustic detection component pass through the rock plate and are received by an acoustic reception assembly. The confining pressure pump applies a confining pressure on the plate model. The pipeline component includes an inner pipeline and an outer pipeline, and a fluid is provided between the outer and the inner pipelines. Cables of the acoustic detection component are provided inside the inner pipeline and are connected to the outside through the inner pipeline.

20 Claims, 8 Drawing Sheets

28

50

30

2

DISPLACEMENT DEVICES

CROSS-REFERENCE TO RELATED APPLICATIONS

This application claims priority to Chinese Patent Application No. 202310370523.4, filed on Apr. 10, 2023, the entire contents of which are hereby incorporated by reference.

TECHNICAL FIELD

The present disclosure relates to the field of oil and gas exploration, and in particular, to displacement devices.

BACKGROUND

Currently, most of indoor experiments in the field of oil and gas are simulation experiments of plunger cores and sand-filled models. For non-homogeneous oil and gas reservoirs, usual plunger cores and full-diameter cores are unable to simulate the dynamic characteristics of the real oil and gas reservoirs. Therefore, artificial plate models or natural cores are needed for simulation experiments. A core holder of the plate model may be used in simulation experiments of oil reservoirs such as non-homogeneity, injection and extraction from different well networks, high-pressure replacement of low-permeability reservoirs, etc. However, there are still some difficulties that lead to inaccurate results of simulation experiments.

First, it is difficult to simulate a real underlying environment. The plate model is larger than the ordinary core. The larger the plate model, the lower the bearing pressure, thus the current plate model is unable to simulate stratigraphic temperature and pressure conditions of high-pressure or ultra-high-pressure oil and gas reservoirs.

Secondly, it is difficult to get real data. The currently used detection system relies on transverse and longitudinal slides and motors to drive the detector to scan the plate model. However, under the high temperature and pressure conditions inside the cylinder, signal lines and wires are easily damaged by the high temperature and pressure of the internal hydraulic oil, which is dangerous. Besides, the scanning takes a long time, and cannot accurately respond to a fluid distribution within an intact rock plate at a certain moment.

Third, the plate model is not sealed enough. Existing plate model detection requires electrodes to be set up above and below the rock plate to send and receive signals, which makes the plate model less hermetic. To improve the sealing performance, it is common to apply a sealant to the plate model. However, the sealant tends to fail under high temperature and pressure, resulting in insufficient sealing performance of the plate model.

Therefore, it is desired to provide a displacement device, which can effectively improve the ability of a plurality of components in the displacement device to withstand high temperatures and high pressures and enhance the sealing performance of a plate model, thereby enhancing the experimental reliability of the displacement device.

SUMMARY

The purpose of the present disclosure is to provide a displacement device, which is simple in principle, convenient in operation, and accurate in measurement. The displacement device can simulate the development of oil and gas reservoirs with a strong non-homogeneity and realize real underground conditions of the development of oil and gas reservoirs that can not be simulated by ordinary cores such as the deployment of injection and extraction well networks. In order to achieve the above purpose, the present disclosure adopts the following technical solutions.

One or more embodiments in the present disclosure provide a displacement device including a plate model, a cylinder, a circulation component, a displacement component, a confining pressure pump, and a pipeline component. The plate model may include a model cavity and a rock plate disposed within the model cavity. A sealing member may be provided on an outer surface of the model cavity, at least one electrode sheet may be embedded in the sealing member, and the rock plate may be sealed by the sealing member and the model cavity. An injection pipeline and a discharge pipeline may be inserted at opposite ends of the rock plate, respectively. The cylinder may be provided with cover plates at two ends along an axial direction. A first cover plate in the cover plates may be provided with a first injection port, a second injection port, and a second discharge port, a second cover plate in the cover plates may be provided with a first discharge port, and the first injection port and the first discharge port may be connected to an interior of the cylinder. The second injection port may be connected to the injection pipeline, and the second discharge port may be connected to the discharge pipeline. The circulation component may include a pressurized pump and a pressurized pipeline. A first end of the pressurized pipeline may be connected to the first injection port, a second end of the pressurized pipeline may be connected to the first discharge port, the pressurized pipeline may be connected to the pressurized pump at a location close to the second end of the pressurized pipeline by a pipeline branch, and the pressurized pump may pressurize a fluid in the pressurized pipeline. The confining pressure pump may be connected to the second end of the pressurized pipeline. The confining pressure pump may drive a pressurized fluid inside the pressurized pipeline to be injected into the interior of the cylinder from the first injection port to exert a confining pressure on the plate model. The displacement component may include a displacement pump and at least one displacement medium container. The at least one displacement medium container may be connected to the second injection port through a displacement pipeline. The displacement pump may drive a displacement medium inside the at least one displacement medium container to be injected into the rock plate from the second injection port. The acoustic detection component may include an acoustic emission assembly and an acoustic reception assembly. The acoustic emission assembly and the acoustic reception assembly may be disposed in parallel on both sides of the plate model, and an acoustic signal generated by the acoustic emission assembly may pass through the rock plate through the at least one electrode sheet and may be received by the acoustic reception assembly. The pipeline component may include an inner pipeline and an outer pipeline sleeved over the inner pipeline. A fluid may be provided between the outer pipeline and the inner pipeline, and the inner pipeline may be internally configured to thread cables.

In some embodiments, the at least one displacement medium container may include a gaseous medium container, a water medium container, and an oil medium container, and the displacement pipeline may be provided with a first valve, a second valve, and a third valves. A gaseous medium inside the gaseous medium container may be injected into the rock plate from the second injection port through a cooperation between the displacement pump and the first valve. A water medium inside the water medium container may be injected into the rock plate from the second injection port through a cooperation between the displacement pump and the second valve. An oil medium inside the oil medium container may be injected into the rock plate from the second injection port through a cooperation between the displacement pump and the third valve.

In some embodiments, the displacement device further comprises a return pressure assembly. The return pressure assembly may include a return pressure pump and a return pressure pipeline. A first end of the return pressure pipeline may be connected to the return pressure pump. A second end of the return pressure pipeline may be connected to the second discharge port. The return pressure pipeline may be provided with a fourth valve and a return pressure medium container at an end near the return pressure pump. A return pressure medium may be injected from the return pressure medium container into the interior of the cylinder from the second discharge port through a cooperation between the return pressure pump and the fourth valve.

In some embodiments, a pressure gauge may be provided on the displacement pipeline near the second injection port, a first pressure sensor may be provided on the pressurized pipeline near the first discharge port, and/or a second pressure sensor may be provided on the return pressure pipeline near the second discharge port.

In some embodiments, the pressurized pipeline may be sleeved with a heating coil, and the heating coil may heat the fluid inside the pressurized pipeline.

In some embodiments, the sealing member may include a contact layer, a spacer layer, and a pressure-bearing layer. The spacer layer may be disposed between the contact layer and the pressure-bearing layer, and the contact layer may be disposed in contact with the rock plate.

In some embodiments, a contact area of the spacer layer may be smaller than a contact area of the contact layer and a contact area of the pressure-bearing layer, respectively, so that a gap may be formed between the contact layer and the pressure-bearing layer.

In some embodiments, the acoustic emission assembly may include an emitter, a guide rail, and a pulley, the emitter may be disposed on the pulley, and the pulley may be disposed in the guide rail. The acoustic reception assembly may include a receiver and a receiving plate, the receiver may be disposed on the receiving plate, the receiving plate is mounted with rollers, and the rollers may be embedded in an inner wall of the cylinder.

In some embodiments, the guide rail may be connected to a telescopic rod, and the telescopic rod may include an inner threaded rod and an outer threaded rod. The outer threaded rod may be electrically connected to a first motor, and the outer threaded rod may be driven to rotate by the first motor to move the acoustic emission assembly.

In some embodiments, the first cover plate may be provided with a first support assembly on a side facing the interior of the cylinder, the second cover plate may be provided with a second support assembly on a side facing the interior of the cylinder, and the plate model may be fixed to the interior of the cylinder by a cooperation between the first support assembly and the second support assembly.

In some embodiments, the first cover plate may be detachably connected with the cylinder.

The embodiment of the present disclosure provides a displacement device with a simple experimental principle and easy operation. By setting an acoustic wave transmitting and receiving device inside the cylinder and connecting the plate model to the cover plate, the installation is convenient. High-pressure-resistant pipes are provided inside the cylinder to isolate the signal line from the pressurized fluid, which makes the signal line less likely to be damaged. By setting up a sealing member with a three-layer structure, the differential pressure sealing effect may be better, which provides a reliable high temperature and high pressure large-scale modeling displacement device for experiments of sweep efficiency and non-homogeneity, etc., of the oil and gas reservoir displacement development.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

Figure 1:
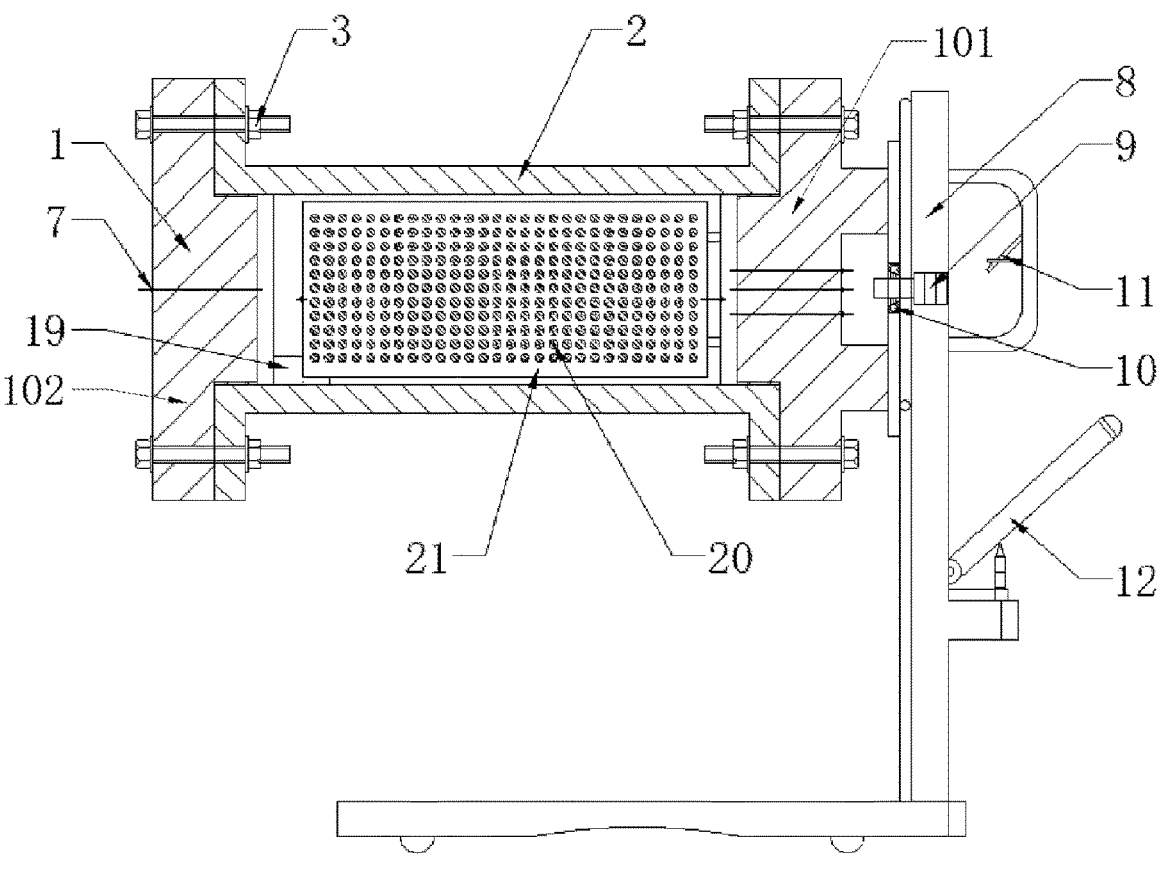
FIG. 1 is a diagram illustrating a main view of a displacement device according to some embodiments of the present disclosure.

Description of markers in the accompanying drawings: 1, cover plate; 101, first cover plate; 102, second cover plate; 2, cylinder; 3, bolt; 4, first injection port; 5, second injection port; 6, second discharge port; 7, first discharge port; 8, forklift; 9, second motor; 10, bearing; 11, brake handle; 12, lift handle; 13, support ring; 14, injection pipeline; 15, discharge pipeline; 16, rock plate; 17, model cavity; 18, support plate; 19, support block; 20, electrode sheet; 21, pressure-bearing layer; 22, contact layer; 23, contact layer; 24, telescopic rod; 25, guide rail; 26, pulley; 27, emitter; 28, receiving plate; 29, receiver; 30, roller; 31, pipeline component; 311, inner pipeline; 312, outer pipeline; 32, pressurized pump; 33, pressurized valve; 34, heating coil; 35, temperature-sensitive element; 36, pressurized pipeline; 37, displacement pump; 38, oil medium container; 39, water medium container; 40, gaseous medium container; 41, discharge valve; 42, pressure gauge; 43, confining pressure pump; 44, circulation component; 45, plate model; 46, return pressure pump; 47, return pressure medium container; 48, fourth valve; 49, processor; 50, slide; 51, return pressure pipeline; 52, pressure sensor; 53, flowrate regulating assembly; 54, gas flowmeter; 55, first motor; 56, third valve; 57, second valve; 58; first valve.

DETAILED DESCRIPTION

To more clearly illustrate the technical solutions related to the embodiments of the present disclosure, a brief introduction of the drawings referred to the description of the embodiments is provided below. Obviously, the drawings described below are only some examples or embodiments of the present disclosure. Those having ordinary skills in the art, without further creative efforts, may apply the present disclosure to other similar scenarios according to these drawings. Unless obviously obtained from the context or the context illustrates otherwise, the same numeral in the drawings refers to the same structure or operation.

It should be understood that "system", "device", "unit" and/or "module" as used herein is a manner used to distinguish different components, elements, parts, sections, or assemblies at different levels. However, if other words serve the same purpose, the words may be replaced by other expressions.

In the existing technology, the technology related to the displacement device may be referred to in the patent document with Publication No. CN 201555791 U (A core holder of a multi-layer plate model), which may withstand a temperature of 100° C. and a pressure of 25 MPa and may be unable to simulate the formation temperature and pressure conditions of a high-pressure, ultra-high-pressure oil and gas reservoir.

As another example, the patent document with Publication No. CN 112816394 A (A three-phase saturation testing device and method for high-temperature and high-pressure plate model oil, gas, and water), discloses that a detection system relies on the transverse and longitudinal slides and motors to drive the detector to carry out a zigzag walking location to complete the scanning of the entire rock plate. The detection system moves under a high-temperature and high-pressure hydraulic oil environment, the signal line and wire have a short service life, and the scanning time is long, which cannot accurately reflect the internal fluid distribution of the complete rock plate at a certain moment.

As yet another example, the patent document with Publication No. CN 112255253 (High temperature and high pressure large-scale dynamic X-ray scanning experimental device for oil and water repulsion), discloses that the rock plate is fastened by threads, sealing is applied to the top and bottom of the rock plate by applying sealing glue, and helium is used as a peripheral pressurizing medium. However, the pressurizing medium of the gas is difficult to control, the pressure is unstable, and the top and bottom of the core coated with a layer of sealing glue may cause a failure of the sealing in the presence of high temperatures and high pressures.

In view of the foregoing, some embodiments of the present disclosure provide a displacement device, which is simple in principle, convenient in operation, and accurate in measurement. The displacement device can simulate the development of oil and gas reservoirs with a strong non-homogeneity and realize real underground conditions of the development of oil and gas reservoirs that can not be simulated by ordinary cores such as the deployment of injection and extraction well networks.

Figure 2:
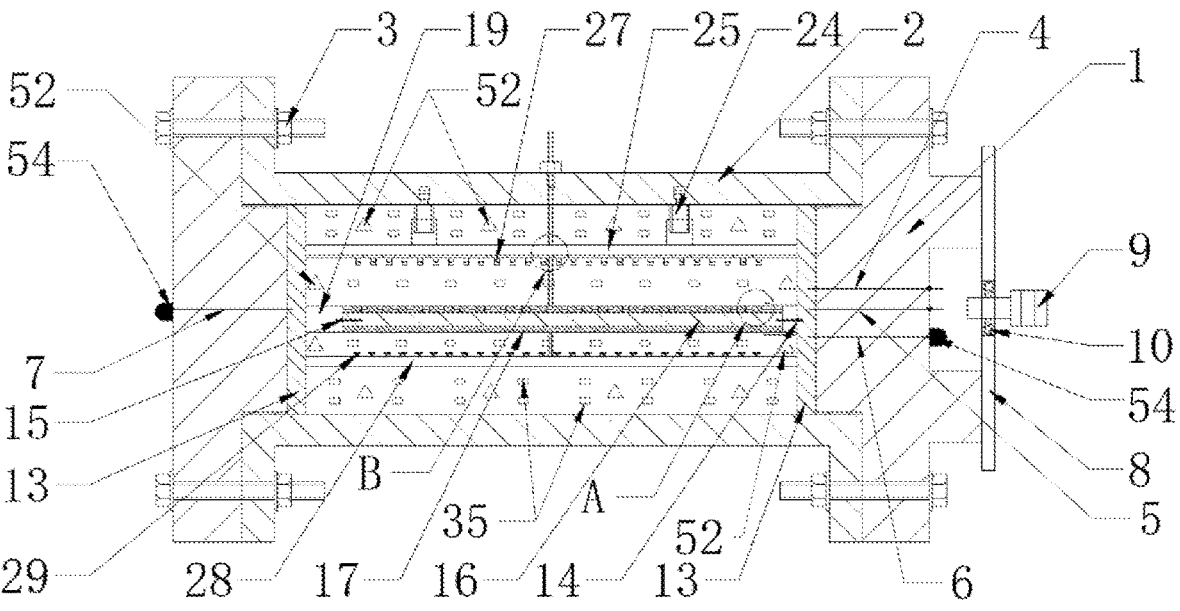
FIG. 2 is a diagram illustrating a top view of a displacement device according to some embodiments of the present disclosure.
Figure 3:
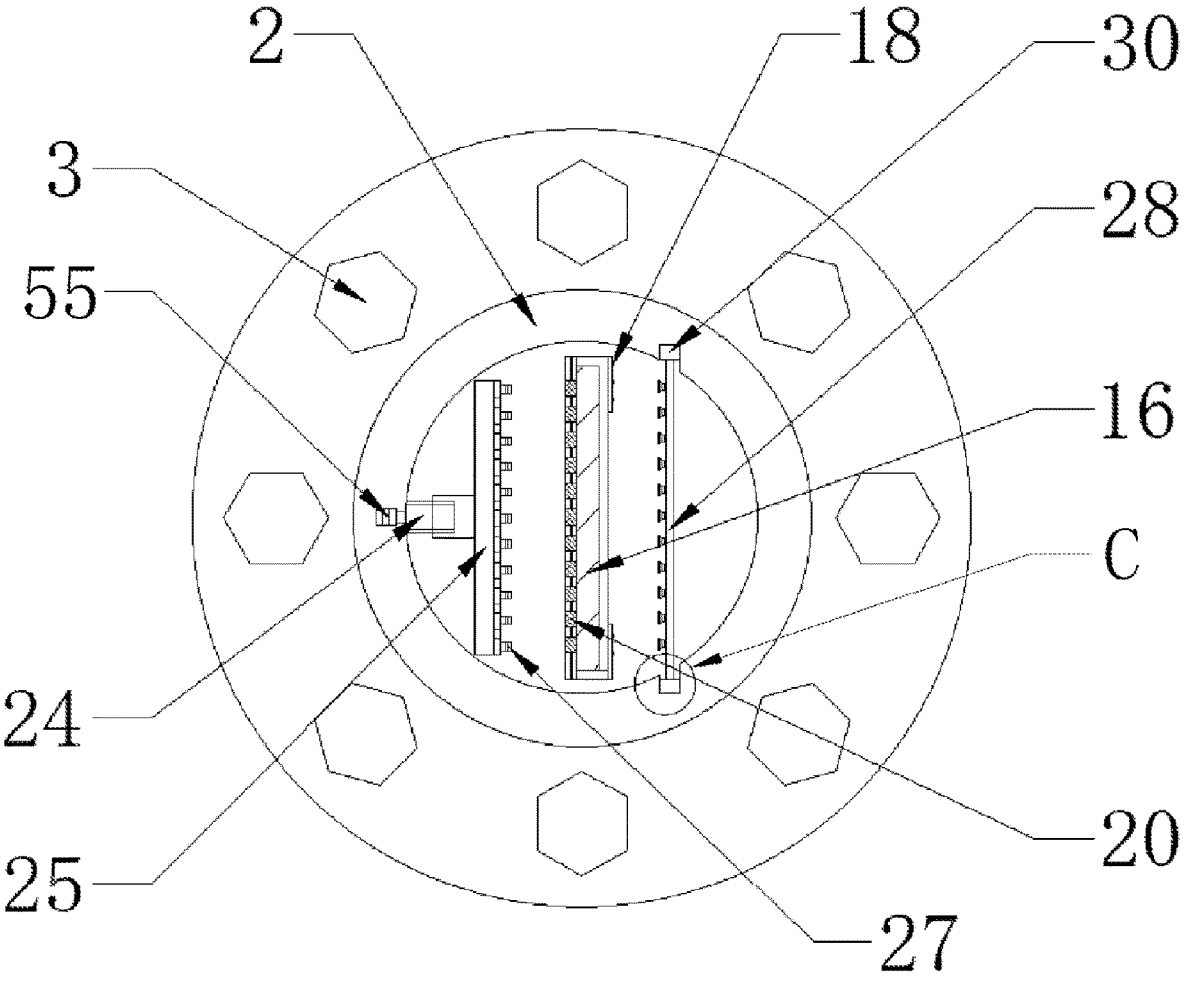
FIG. 3 is a diagram illustrating a side view of a displacement device according to some embodiments of the present disclosure.

FIG. 1 is a diagram illustrating a main view of a displacement device according to some embodiments of the present disclosure. FIG. 2 is a diagram illustrating a top view of a displacement device according to some embodiments of the present disclosure. FIG. 3 is a diagram illustrating a side view of a displacement device according to some embodiments of the present disclosure.

As shown in FIGS. 1-3, in some embodiments, the displacement device may include a plate model 45, a cylinder 2, a circulation component 44, a confining pressure pump 43, a displacement component, an acoustic detection component, and a pipeline component 31. The plate model 45 and the acoustic detection component are disposed within the cylinder 2.

The plate model 45 is a component for simulating the strata in a displacement experiment. In some embodiments, the plate model 45 may include a model cavity 17 and a rock plate 16 disposed within the model cavity 17.

The model cavity 17 refers to a cavity in which the rock plate 16 is placed. In some embodiments, the model cavity 17 may be a box with an open top. The model cavity 17 may be made of a plurality of materials, for example, a material that is resistant to heat and pressure, such as metal or stone. In some embodiments, the model cavity 17 may be made of iron or an alloy thereof.

In some embodiments, the rock plate 16 may be a natural rock plate 16, obtained from a formation. In some embodiments, the rock plate 16 may be artificially fabricated to simulate a structure of a real formation.

In some embodiments, a sand filling scheme may be determined based on relevant core data provided at an oilfield site, and the fabricated sand filling model may be designated as a small piece of plunger core to determine the permeability, porosity, and other physical parameters of the rock. If the parameters satisfy experimental requirements, the fabricated sand filling model may be filled into the model cavity 17 as the rock plate 16.

As shown in FIG. 1 and FIG. 2, in some embodiments, the injection pipeline 14 and the discharge pipeline 15 may be inserted at opposite ends of the rock plate 16. One end of the injection pipeline 14 may be inserted into the rock plate 16, and another end of the injection pipeline 14 may be connected to a second injection port 5 on the first cover plate 101, and the injection pipeline 14 may be configured to inject liquids and/or gases into an interior of the rock plate 16. One end of the discharge pipeline 15 may be inserted into the rock plate 16, and another end of the discharge pipeline 15 may be connected to the second discharge port 6 on the first cover plate 101. The discharge pipeline 15 may be configured to discharge liquids and/or gases inside the rock plate 16.

As shown in FIG. 1 and FIG. 3, in some embodiments, a sealing member may be provided on an outer surface of the model cavity 17, and at least one electrode sheet 20 may be embedded in the sealing member.

The sealing member refers to a member configured to seal the rock plate 16 within the model cavity 17. In some embodiments, the sealing member may be affixed to an opening on a top of the model cavity 17, and an edge of the sealing member may be tightly fitted to an edge of the opening on the top of the model cavity 17 to seal the rock plate 16 inside the model cavity 17.

The sealing member may include a plurality of materials, such as heat-resistant rubber, silicone, or the like. In some embodiments, the sealing member may be connected to the model cavity 17 based on the material properties thereof, e.g., bonded to the model cavity 17 after hot melting. In some embodiments, an adhesive layer (e.g., glue, adhesive tape) may also be provided at a bottom of the sealing member to bond the sealing member to the model cavity 17 via the adhesive layer.

Figure 5:
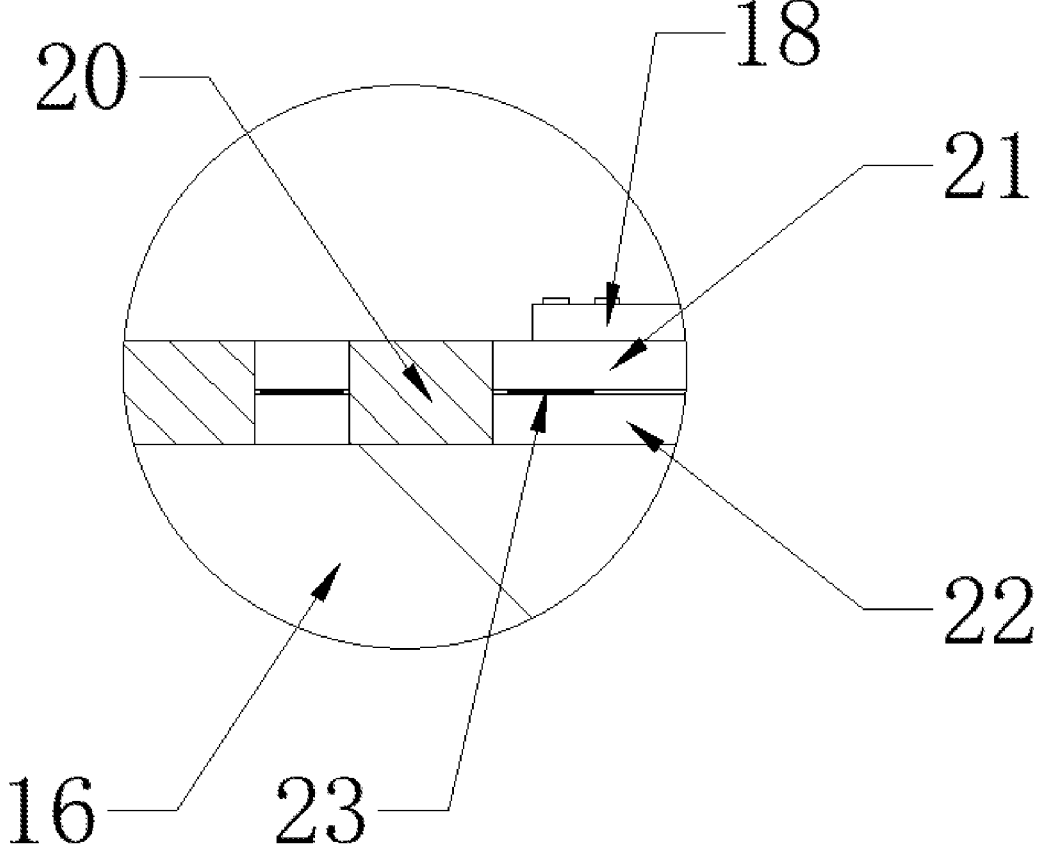
FIG. 5 is a diagram illustrating an enlarged view at A in FIG. 2 according to some embodiments of the present disclosure.

As shown in FIG. 5, in some embodiments, the sealing member may be of a multilayer structure including a contact layer 22, a spacer layer 23, and a pressure-bearing layer 21.

The spacer layer 23 may be disposed between the contact layer 22 and the pressure-bearing layer 21, and the contact layer 22 may be in contact with the rock plate 16.

In some embodiments, a stiffness of the pressure-bearing layer 21 needs to be greater than that of the contact layer 22, so that when an exterior of the plate model 45 is in a high-pressure environment, an external pressure may press the pressure-bearing layer 21 toward the rock plate 16, thereby pressing the spacer layer 23 and the pressure-bearing layer 21 tightly against the model cavity 17, enhancing a sealing performance of the sealing member by the external pressure of the plate model 45. Meanwhile, the pressure-bearing layer 21, which is more rigid, is less likely to deform when subjected to the external pressure of the plate model 45.

In some embodiments, a contact area of the spacer layer 23 may be smaller than a contact area of the contact layer 22 and a contact area of the pressure-bearing layer 21, respectively, so that a gap may be formed between the contact layer 22 and the pressure-bearing layer 21.

When the contact area of the spacer layer 23 is smaller than the contact area of the contact layer 22 and the contact area of the pressure-bearing layer 21, edges of the contact layer 22 and the pressure-bearing layer 21 may be extended beyond an edge of the spacer layer 23, and the gap may be formed at the edges of the contact layer 22 and the pressure-bearing layer 21. Under the action of the pressure difference between the interior of the model cavity 17 and the outside environment, it is possible to make the sealing member always fit with a part to be sealed, so that the sealing effect may be better.

As shown in FIG. 5, in some embodiments, a plurality of electrode sheets 20 may be embedded in the sealing member. The electrode sheets 20 may be of a plurality of materials, e.g., metal, etc. In some embodiments, the material of the model cavity 17 may be the same as the material of the electrode sheet 20.

In some embodiments, for a portion of the sealing member between two adjacent electrode sheets 20, the contact area of the spacer layer 23 therein may be less than the contact area of the contact layer 22 and the contact area of the pressure-bearing layer 21, respectively, so that a gap may be formed between the contact layer 22 and the pressure-bearing layer 21 between the two adjacent electrode sheets 20.

Because there is a gap between the contact layer 22 and the pressure-bearing layer 21, when the sealing member is pressurized, the pressure outside the sealing member may be greater than the pressure in the gap between the contact layer 22 and the pressure-bearing layer 21. Under the action of the pressure difference, the pressure-bearing layer 21 may show a certain degree of bending deformation, which can in turn enhance the sealing effect of the sealing member on the model cavity 17.

The cylinder 2 refers to a container of the displacement device. The cylinder 2 may be a cylinder of a plurality of shapes, such as square, triangular, circular, etc.

As shown in FIG. 1 and FIG. 2, in some embodiments, the cylinder 2 is provided with cover plates 1 at two ends along an axial direction. A first cover 101 in the cover plates 1 is provided with a first injection port 4, a second injection port 5, and a second discharge port 6. A second cover 102 in the cover plates 1 is provided with a first discharge port 7, and the first injection port 4 and the first discharge port 7 are connected to the interior of the cylinder 2, the second injection port 5 is connected to the injection pipeline 14, and the second discharge port 6 is connected to the discharge pipeline 15.

The cover plates 1 refer to parts that seal the cylinder 2. In some embodiments, the cover plates 1 are provided with a sealing rubber ring to prevent leakage of liquid inside the cylinder 2. In some embodiments, the cover plate 1 may be provided with a rubber buffer block, and the rubber buffer block may play a buffering role in the process of installing or removing the plate model 45, avoiding deformation and damage to the pipeline, the inlet, and the outlet caused by accidental touching. In some embodiments, a surface of the plate model 45 may include a rubberized skin (not shown in the accompanying drawings) that matches the rubber buffer block. In some embodiments, a shape of the rubberized skin may be associated with a shape of the rubber buffer block.

The first injection port 4 refers to an inlet for inputting a confining pressure into the interior of the cylinder 2. The confining pressure refers to a pressure applied to the plate model 45. The first discharge port 7 refers to an outlet for discharging liquids and/or gases from the interior of the cylinder 2.

In some embodiments, gases and/or liquids may be injected into the interior of the cylinder 2 through the first injection port 4, and gases and/or liquids may be discharged from the interior of the cylinder 2 through the first discharge port 7.

The second injection port 5 refers to an inlet for inputting liquids and/or gases into an interior of the plate model 45. The second injection port 5 may be connected to the injection pipeline 14, and the liquids and/or gases may be input from the second injection port 5 to be injected into the interior of the plate model 45 via the injection pipeline 14. By inputting the gas into the interior of the plate model 45, an internal pressure in the plate model 45 may be increased.

The second discharge port 6 refers to an outlet for discharging liquids and/or gases from the interior of the plate model 45. The second discharge port 6 may be connected to the discharge pipeline 15, the liquids and/or gases may be output via the discharge pipeline 15 and may be discharged to the outside of the cylinder 2 via the second discharge port 6.

Through the cooperation between the second injection port 5, the second discharge port 6, the injection pipeline 14, and the discharge pipeline 15, it is possible to carry out a displacement experiment.

In some embodiments, the cover plate 1 may be detachably connected to the cylinder 2. The detachable connection may be performed in a plurality of manners, such as a threaded connection, a bolt connection, etc. For example, the first cover plate 101 and/or the second cover plate 102 may be connected to the cylinder 2 by a bolt 3.

In some embodiments, a first support assembly may be provided on a side of the first cover plate 101 facing the interior of the cylinder 2 (i.e., an inner side), and a second support assembly may be provided on the side of the second cover plate 102 facing the interior of the cylinder 2. By the cooperation of the first support assembly and the second support assembly, it is possible to fix the plate model 45 in the interior of the cylinder 2.

In some embodiments, the first support assembly may include a support ring 13 and a support plate 18, and the second support assembly may include a support ring 13 and a support block 19.

The support ring 13 may be in a plurality of forms. For example, a steel ring, etc. In some embodiments, the support ring 13 may be fixedly connected to the first cover plate 101 and the second cover plate 102 in a plurality of ways. For example, the support ring 13 may be embedded in inner sides of the first cover plate 101 and the second cover plate 102, or the support ring 13 may also be connected to the inner side of the first cover plate 101 and the second cover plate 102 via a fastener.

The support plate 18 refers to a plate-like structure that acts as a support. The support block 19 refers to a block-like structure that acts as a support. The support plate 18 and the support block 19 are fixedly connected to the support ring 13, respectively.

In some embodiments, one side of the plate model 45 may be placed on the support block 19 and another side of the plate model 45 may be placed on the support plate 18.

In some embodiments, the support plate 18 and the support block 19 may be placed on an inner wall of the cylinder 2 to fix the plate model 45 to the interior of the cylinder 2, enabling the plate model 45 to be evenly stressed and securely installed.

In some embodiments, there may be two support plates 18, the two support plates 18 may be fixed to the support ring 13 of the first cover plate 101. In some embodiments, one support plate 18 may be provided at each location where the first cover plate 101 contacts the inner wall of the cylinder 2 to allow the two support plates 18 to clamp the plate model 45.

The circulation component 44 refers to a component that injects fluid into the interior of cylinder 2.

In some embodiments, the circulation component 44 may include a pressurized pump 32 and a pressurized pipeline 36. A first end of the pressurized pipeline 36 may be connected to the first injection port 4, a second end of the pressurized pipeline 36 may be connected to the first discharge port 7, the pressurized pipeline 36 may be connected to the pressurized pump 32 at a location close to the second end of the pressurized pipeline 36 by a pipeline branch, and the pressurized pump 32 may pressurize a fluid in the pressurized pipeline 36.

In some embodiments, the first end of the pressurized pipeline 36 may be a location where the fluid flows out of the pressurized pipeline 36, and the second end of the pressurized pipeline 36 may be a location where the fluid flows into the pressurized pipeline 36. In other words, the fluid in the pressurized pipeline 36 flows from the second end to the first end.

In some embodiments, connecting the first end of the pressurized pipeline 36 to the first injection port 4 enables the fluid within the pressurized pipeline 36 to be injected into the interior of the cylinder 2 through the first injection port 4. Connecting the second end of the pressurized pipeline 36 to the first discharge port 7 enables the fluid within the cylinder 2 to be returned to the pressurized pipeline 36 through the first discharge port 7, creating a circulation.

Figure 4:
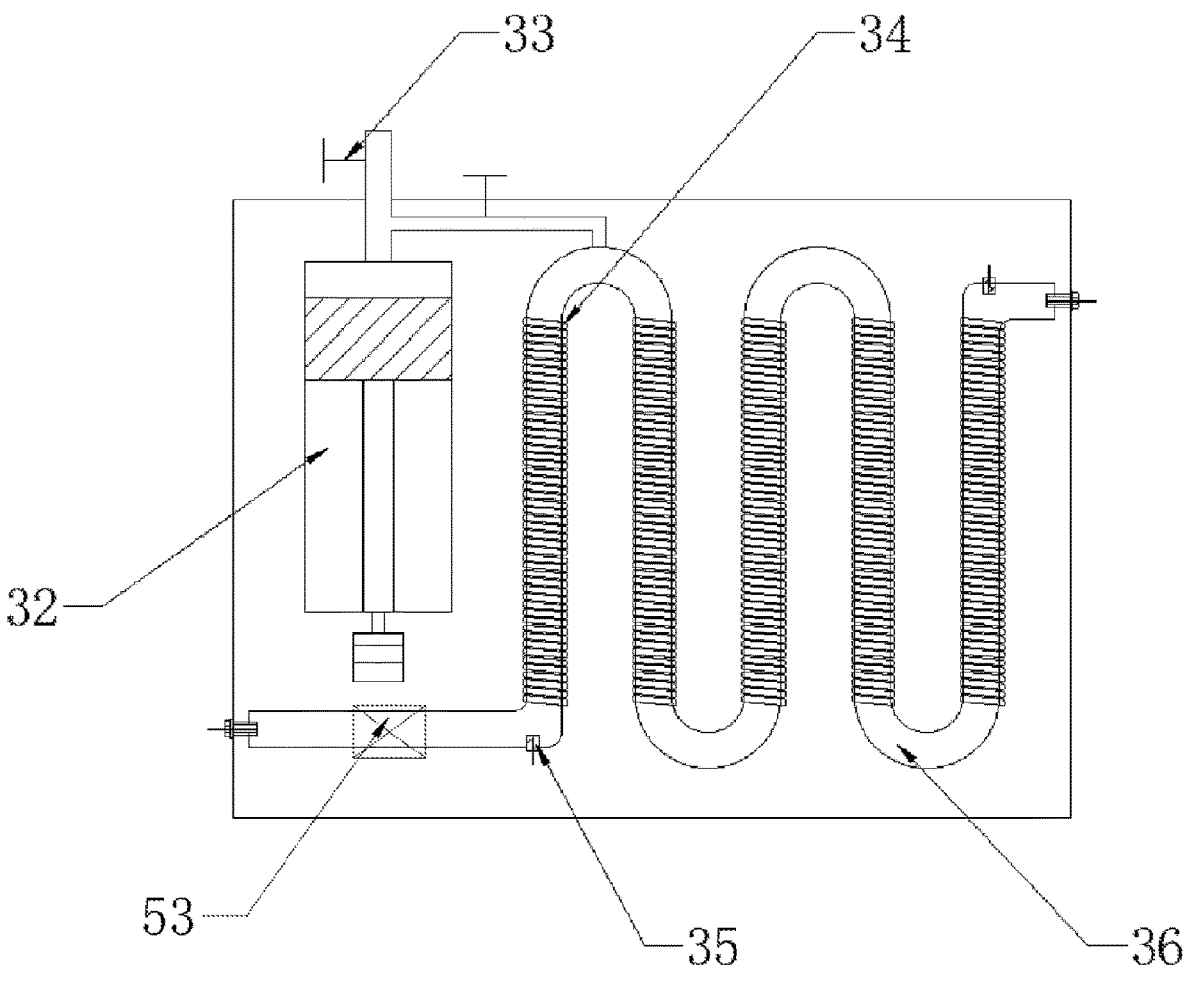
FIG. 4 is a schematic diagram illustrating an exemplary structure of a circulation component according to some embodiments of the present disclosure.

The pressurized pump 32 pressurizes the fluid within the pressurized pipeline 36. For example, the pressurized pump 32 may be a gas-air pressurized pump, a gas-liquid pressurized pump, etc. As shown in FIG. 4, the pressurized pump 32 may be connected to a location on the pressurized pipeline 36 near the second end via the pipeline branch. The fluid in the pressurized pipeline 36 flows from the second end to the first end, making the pressurized pump 32 provided at a location near the second end of the pressurized pipeline 36, which may help to ensure pressurization effect of the fluid in the pressurized pipeline 36.

In some embodiments, a pressurized valve 33 may be provided on the pipeline branch where the pressurized pump 32 is connected to the pressurized pipeline 36. The pressurized valve 33 is configured to control a pressurization operation of the fluid within the pressurized pipeline 36. When the pressurized valve 33 is open, the fluid within the pressurized pipeline 36 is pressurized. Conversely, the fluid within the pressurized pipeline 36 is not pressurized.

In some embodiments, the pressurized pipeline 36 may be sleeved with a heating coil 34, and the heating coil 34 may heat the fluid within the pressurized pipeline 36. In some embodiments, the heating coil 34 may be a resistance wire, and the heating coil 34 may be heated by energizing the heating coil 34 to heat the heating coil 34, thereby heating the fluid inside the pressurized pipeline 36.

In some embodiments, the fluid inside the pressurized pipeline 36 may be hydraulic oil. The hydraulic oil has good incompressibility and thermal conductivity and may transfer the pressure well while rapidly transferring heat from the heating coil 34 to the interior of the cylinder 2, reducing the temperature difference at the circulation component 44 and a plurality of locations within the cylinder 2, so that the temperature inside the cylinder 2 may be stabilized and controlled.

It should be noted that, when carrying out the displacement experiment, connecting the first end of the pressurized pipeline 36 to the first injection port 4 and connecting the second end of the pressurized pipeline 36 to the first discharge port 7 may realize the circulation of the fluid inside the cylinder 2 and the pressurized pipeline 36. Before carrying out the displacement experiment, only the first end of the pressurized pipeline 36 may be connected to the first injection port 4, without connecting the second end of the pressurized pipeline 36 to the first discharge port 7, to evacuate the gas inside the cylinder 2 by injecting the fluid into the cylinder 2. After the gas inside the cylinder 2 is evacuated, the second end of the pressurized pipeline 36 may be connected to the first discharge port 7 to test the sealing performance of the cylinder 2. More descriptions regarding testing the sealing performance of the cylinder 2 may be found hereinafter.

The confining pressure pump 43 refers to a component that applies a confining pressure to the interior of the cylinder 2. As shown in FIG. 4, the confining pressure pump 43 is connected to the second end of the pressurized pipeline 36, and the confining pressure pump 43 drives a pressurized fluid or a pressurized and heated fluid inside the pressurized pipeline 36 to be injected into the interior of the cylinder 2 from the first injection port 4 to exert a confining pressure on the plate model 45. In some embodiments, the confining pressure pump 43 may be a peristaltic pump or a centrifugal pump, etc.

In some embodiments, a confining pressure valve may be provided between the confining pressure pump 43 and the pressurized pipeline 36, which allows for a quick start or stop of pressure transfer between the confining pump 43 and the pressurized pipeline 36 by opening or closing the confining pressure valve.

By providing the circulation component 44 and the confining pressure pump 43, it is possible to pressurize and heat the fluid inside the pressurized pipeline 36 and input the pressurized and warmed fluid into the interior of the cylinder 2, to make the fluid circulate in the interior of the cylinder 2 and in the pressurized pipeline 36 to simulate temperature conditions and pressure conditions in the formation.

The displacement component refers to a component that displaces a liquid or gas from the plate model 45 during a displacement experiment.

Figure 8:
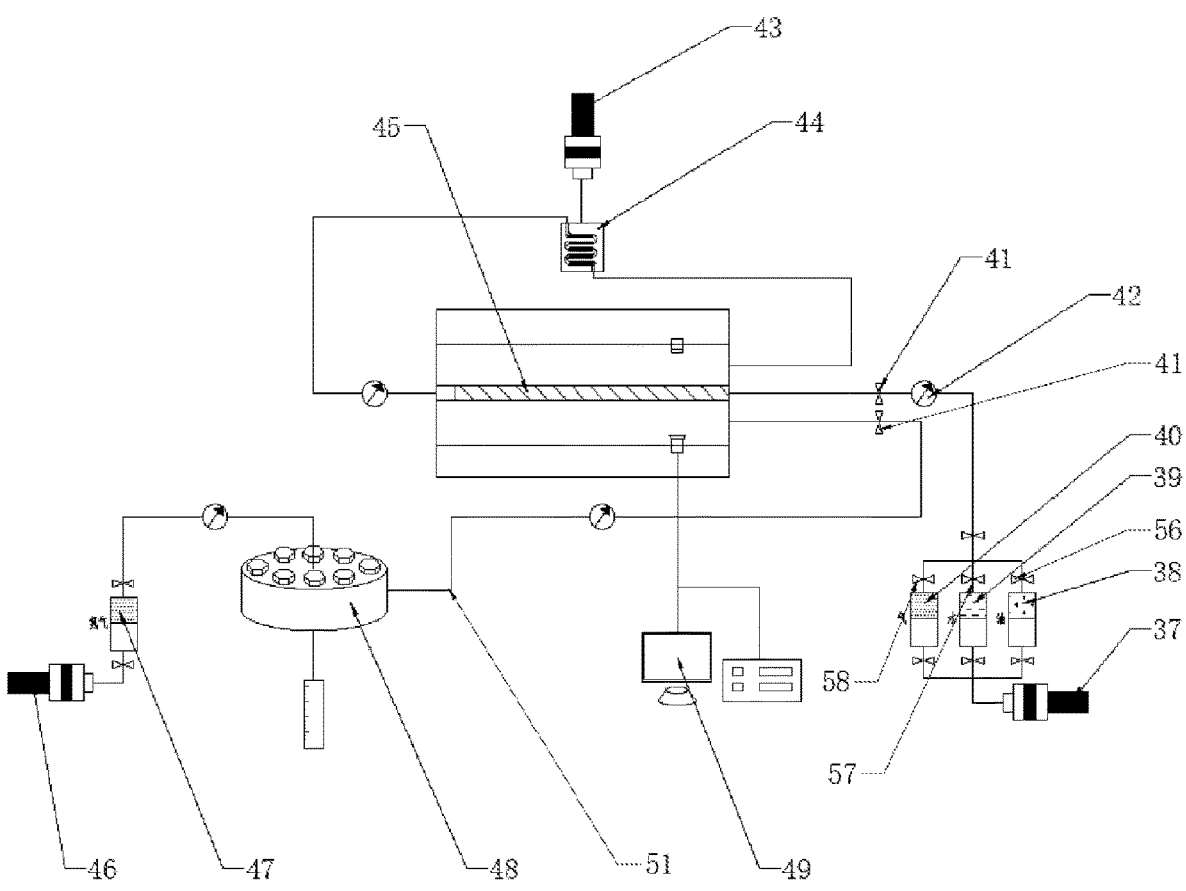
FIG. 8 is a schematic diagram illustrating an experimental scenario of a displacement device according to some embodiments of the present disclosure.

As shown in FIG. 8, in some embodiments, the displacement component may include a displacement pump 37 and at least one displacement medium container. The at least one displacement medium container is connected to the second injection port 5 through a displacement pipeline. The displacement pump may drive a displacement medium inside the at least one displacement medium container to be injected into the rock plate from the second injection port.

The displacement pump 37 refers to a component for injecting a displacement medium from the displacement medium container into the plate model 45. In some embodiments, the displacement pump 37 may be a peristaltic pump or a centrifugal pump, etc.

The displacement pipeline refers to a pipeline for connecting the displacement medium container to the second injection port 5. The displacement pipeline may deliver the displacement medium from the displacement medium container to the second injection port 5. In some embodiments, a delivery valve may be provided on the displacement pipeline to control the delivery process of the displacement medium.

The displacement medium container contains a displacement medium for displacing the fluid within the plate model 45. In some embodiments, the displacement medium container is provided outside of the cylinder 2.

One displacement medium container may be configured to store the same type of displacement medium. There may include one or more displacement medium containers for storing one type of displacement medium.

In some embodiments, the displacement medium includes but is not limited to, one or more of water, gas, oil, or the like.

In some embodiments, the at least one displacement medium container includes a gaseous medium container 40, a water medium container 39, and an oil medium container 38, and the displacement pipeline is provided with a first valve 58, a second valve 57, and a third valve 56. A gaseous medium inside the gaseous medium container 40 is injected into the rock plate 16 from the second injection port 5 through a cooperation between the displacement pump 37 and the first valve 58. A water medium inside the water medium container 39 is injected into the rock plate 16 from the second injection port 5 through a cooperation between the displacement pump 37 and the second valve 57. An oil medium inside the oil medium container 38 is injected into the rock plate 16 from the second injection port 5 through a cooperation between the displacement pump 37 and the third valve 56.

The gaseous medium container 40 is stored with gas. The water medium container 39 is stored with a water medium (e.g., formation water). The oil medium container 38 is stored with the oil medium (e.g., simulated oil). The first valve 58 is configured to control a process for conveying the gaseous medium. The second valve 57 is configured to control a process for conveying the water medium. The third valve 56 is configured to control a process for conveying the gaseous medium.

In some embodiments, a bound water saturation needs to be established in the plate model 45 before conducting the displacement experiment. At this time, the second valve 57 may be controlled to open, the first valve 58 and the third valve 56 may be controlled to close, and the displacement pump 37 may be controlled to inject the water medium in the water medium container 39 into the plate model 45 to simulate the formation water and formation structure binding state.

In some embodiments, during the displacement experiment (e.g., a water oil displacement experiment), the third valve 56 may be controlled to open, the first valve 58 and the second valve 57 may be controlled to close, and the displacement pump 37 may be operated to pump the oil medium in the oil medium container 38 into the plate model 45. When the oil medium is uniformly distributed in the rock plate 16, the third valve 56 may be controlled to close and the second valve 57 may be controlled to open to pump the water medium in the water medium container 39 into the plate model 45 to displace the oil medium in the plate model 45.

In some embodiments, during the displacement experiment (e.g., a gas oil displacement experiment), the third valve 56 may be controlled to open, the first valve 58 and the second valve 57 may be controlled to close, and the displacement pump 37 may be operated to pump the oil medium in the oil medium container 38 into the plate model 45. When the oil medium is uniformly distributed in the rock plate 16, the third valve 56 may be controlled to close and the first valve 58 may be controlled to open to pump the gaseous medium in the gaseous medium container 40 into the plate model 45 to displace the oil medium in the plate model 45. More descriptions regarding the displacement experiment may be found in related descriptions hereinafter.

The acoustic detection component refers to a component that detects a fluid distribution in the plate model 45.

As shown in FIG. 2 and FIG. 3, in some embodiments, the acoustic detection component may include an acoustic emission assembly and an acoustic reception assembly. The acoustic emission assembly and the acoustic reception assembly are disposed in parallel on both sides of the plate model 45, and an acoustic signal generated by the acoustic emission assembly passes through the rock plate 16 through the at least one electrode sheet 20 and is received by the acoustic reception assembly.

The acoustic emission assembly refers to a component for generating an acoustic signal (e.g., an ultrasonic signal, etc.). The acoustic reception assembly refers to a component for receiving the acoustic signal.

As shown in FIG. 3, in some embodiments, the acoustic emission assembly may be disposed on one side of the plate model 45 provided with the electrode sheet 20, and the acoustic reception assembly may be disposed on the opposite side of the plate model 45 provided with the electrode sheet 20.

The acoustic detection component performs detection based on the principle of sonic logging. The acoustic wave emission component transmits acoustic waves to the plate model 45, and the acoustic waves pass through the electrode sheet 20 and then pass through the rock plate 16 to be received by the acoustic reception component. Due to the interaction of fluids and solids, etc., in the rock plate 16, the propagation speed of the acoustic waves may be affected. Based on the acoustic time difference of the dry core, saturated water core, saturated gas core, and saturated oil core analyzed before the start of the experiment, compared with the acoustic time difference measured at the time of the displacement, the saturation of the different locations of the rock plate 16 may be analyzed. The results may be used to visualize the real-time saturation changes in the flat core, which may be used to study the laws of the experiment such as plate sweep efficiency, etc.

Figure 6:
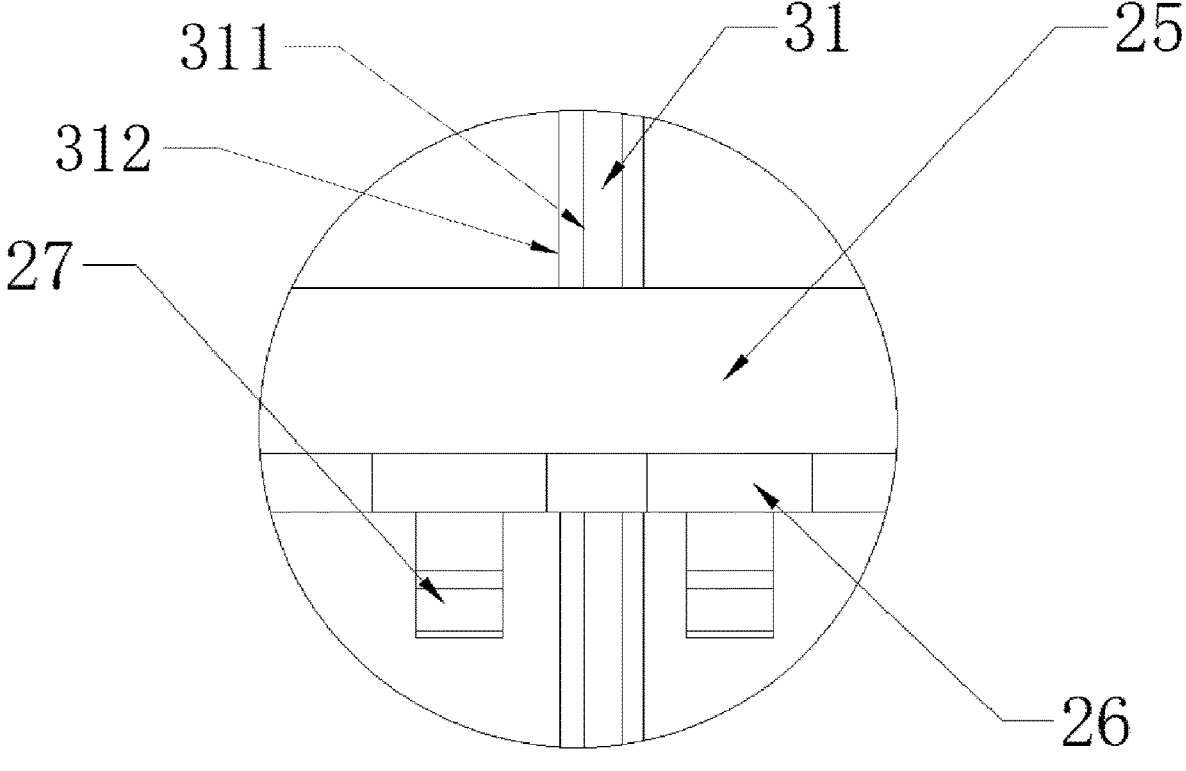
FIG. 6 is a diagram illustrating an enlarged view at B in FIG. 2 according to some embodiments of the present disclosure.
Figure 7:
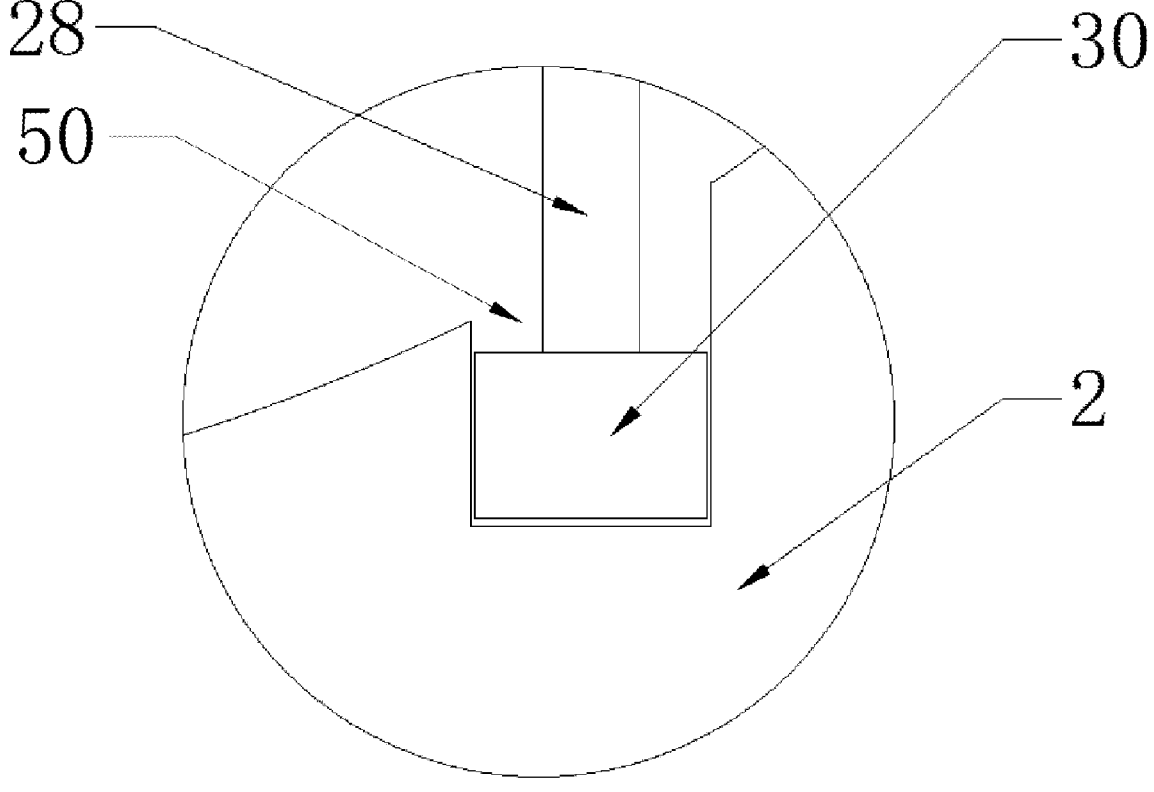
FIG. 7 is a diagram illustrating an enlarged view at C in FIG. 3 according to some embodiments of the present disclosure.

As shown in FIG. 3, FIG. 5, and FIG. 6, in some embodiments, the acoustic emission assembly may include an emitter 27, a guide rail 25, and a pulley 26. The emitter 27 may be disposed on the pulley 26, and the pulley 26 may be disposed in the guide rail 25. The acoustic reception assembly may include a receiver 29 and a receiving plate 28. The receiver 29 may be disposed on the receiving plate 28, the receiving plate 28 may be mounted with rollers 30, and the rollers 30 and the guide rail 25 may be embedded in an inner wall of the cylinder 2.

In some embodiments, the emitter 27, after receiving an electrical signal from the controller, may generate a corresponding acoustic signal based on the characteristics of the signal (e.g., frequency, amplitude, duration).

In some embodiments, when the acoustic wave passes through the plate model 45 and arrives at the receiving plate 28, the receiver 29 on the receiving plate 28 may sense the pressure changes caused by the acoustic signal and convert the changes into the electrical signal for data collection on the scanned acoustic waves.

In some embodiments, a plurality of emitters 27 may be provided on the pulley 26, a count of which corresponds to a count of the electrode sheets 20. The receiving plate 28 is fitted with a plurality of receivers 29, a count of which corresponds to the count of the electrode sheets 20.

As shown in FIG. 2 and FIG. 3, in some embodiments, an extension direction of the guide rail 25 may be parallel to an axial direction of the cylinder 2, allowing the emitter 27 to be moved in the axial direction along the cylinder 2 through the pulley 26 and the guide rail 25. The extension direction of the receiving plate 28 is parallel to the axial direction of the cylinder 2, the receiving plate 28 is provided with the roller 30 at twp ends along an axis of the cylinder 2. The inner wall of the cylinder 2 may be provided with the slide 50 corresponding to the roller 30 in the axial direction, which enables the receiving plate 28 to be moved along the axial direction of the cylinder 2 by the roller 30. In some embodiments, the receiving plate 28 may be translated out of the cylinder 2 along the axial direction of the cylinder 2 to allow for overhauling or replacement of the receiver 29.

Through the pulley 26 and the guide rail 25, it is possible to move the emitter 27 inside the cylinder 2 to the outside of the cylinder 2, making it easy to inspect or replace the emitter 27. By providing the receiving plate 28 on the roller 30, it is possible to pull out or put in the receiving plate 28 along the axial direction of the cylinder 2, facilitating the inspection or replacement of the receiving plate 28.

As shown in FIG. 2, FIG. 3, and FIG. 6, in some embodiments, the guide rail 25 may be connected to a telescopic rod 24. The telescopic rod 24 includes an inner threaded rod and an outer threaded rod. The outer threaded rod is electrically connected to a first motor 55, and the outer threaded rod is driven to rotate by the first motor 55 to move the acoustic emission assembly. In some embodiments, the first motor 55 may be a rotary motor, etc. In some embodiments, the inner threaded rod is fixed to the inner wall of the cylinder 2. The inner threaded rod engages with the outer threaded rod via threads.

When it is necessary to install the plate model 45, and when the first motor 55 drives the outer threaded rod to rotate, the outer threaded rod may be made to move along the threads in a direction close to the first motor 55 while rotating, thus driving the guide rail 25 to move in a direction away from the plate model 45, leaving space inside the cylinder 2 for easy installation of the plate model 45. When the plate model 45 is installed and needs to be subjected to the displacement experiment, an output shaft of the first motor 55 rotates in a reverse direction, driving the outer threaded rod to perform a reversed rotation and move in a direction away from the first motor 55, which in turn drives the guide rail 25 to move in a direction close to the plate model 45 until the guide rail 25 moves to a location that meets the experimental requirements. Through the rotation of the first motor 55 in forward and reverse directions, the guide rail 25 may be driven to move away from or toward the plate model 45, thus adjusting a distance between the acoustic emission assembly and the plate model 45, thereby facilitating the installation of the plate model 45.

In such a case, the whole acoustic reception assembly may be withdrawn and put in from the cylinder 2, which facilitates the inspection and replacement of the receiving plate 28 while leaving more space inside the cylinder 2 for the installation of the plate model 45.

The pipeline component 31 refers to a component that protects cable of the components inside the cylinder 2. As shown in FIG. 6, in some embodiments, the pipeline component 31 may include an inner pipeline 311 and an outer pipeline 312 sleeved over the inner pipeline 311. A fluid is provided between the outer pipeline 312 and the inner pipeline 311, and the inner pipeline 311 is internally configured to thread cables.

In some embodiments, cables of the acoustic detection component, the motor, the displacement pump 37, the pressurized pump 32, and other components may be provided inside of the inner pipeline 311 and connected to the outside through the inner pipeline 311.

In some embodiments, both the inner pipeline 311 and the outer pipeline 312 are pressure-resistant flexible pipelines. For example, a rubber-plastic alloy composite pipeline. The inner pipeline 311 and the outer pipeline 312 may withstand high pressure, and at the same time, have a good bending radius, which allows the equipment in the cylinder 2 to be moved within a certain range, avoiding being affected by high temperatures and high pressures inside the cylinder 2, and reducing the risk of damage to the cables.

In some embodiments, the fluid of the outer pipeline 312 and the inner pipeline 311 may be a low-temperature and high-pressure fluid. In some embodiments, by providing the fluid between the outer pipeline 312 and the inner pipeline 311, high temperatures outside the outer pipeline 312 may be insulated, preventing damage to cables within the inner pipeline 311 at high temperatures. In some embodiments, the distance between the outer pipeline 312 and the inner pipeline 311 is in communication with a cooling device outside the displacement device, and the cooling device may drive cooling fluid therein to flow in the distance between the outer pipeline 312 and the inner pipeline 311 to insulate heat from the pipeline component 31.

In some embodiments, the outer pipeline 312 and the inner pipeline 311 have a radial stiffness that allows the outer pipeline 312 and the inner pipeline 311 to withstand high pressures of the environment within the cylinder 2, preventing damage to the cables from being crushed.

In some embodiments, the outer pipeline 312 and the inner pipeline 311 have an axial flexibility that allows the outer pipeline 312 and the inner pipeline 311 to follow the acoustic detection component as it moves within the cylinder 2.

In some embodiments, the signal line of the electrode sheet 20 is also disposed within the inner pipeline 311 and transmits data obtained therefrom via the signal line to the outside of the displacement device.

In some embodiments, when performing the displacement experiment, a low-temperature and high-pressure fluid with a pressure equal to the confining pressure may be injected into the pipeline component 31. After the temperature of the fluid in the pipeline component 31 rises, the pressure is slightly reduced to allow the fluid to flow out of the pipeline component 31. Subsequently, the pressure is increased, and a cryogenic fluid is injected into the pipeline component 31 to reduce the pipeline temperature.

Some embodiments of the present disclosure include at least the following beneficial effects. (1) The sealing member of the plate model 45 is improved by setting the sealing member into a contact layer 22, a pressure-bearing layer 21, and a spacer layer 23 with different elasticities. An area of the spacer layer 23 is smaller than that of the contact layer 22 and the pressure-bearing layer 21, so there is a pressure difference between the edges of the sealing member and the electrodes when the sealing member is pressurized, which makes the sealing effect better. (2) The time consumed for a single acoustic emitter 27 takes too long to scan back and forth and cannot accurately reflect the liquid flow inside the rock plate 16. By setting a plurality of acoustic emitters 27 and a plurality of acoustic receivers 29, the rock plate 16 may be scanned at the same time, which improves the scanning accuracy and efficiency. (3) The acoustic emission assembly in the cylinder 2 may be moved outside the cylinder 2 through the pulleys 26 and the guide rails 25, which is convenient for checking or replacing the acoustic emission assembly. By setting the telescopic rod 24 that may be telescoped radially along the cylinder 2 above the guide rail 25, the acoustic emission assembly is controlled to telescope radially along the cylinder 2, making it possible to vacate a larger space in the cylinder 2 in the process of installing and removing the plate model 45, which is convenient for the installation of the plate model 45 and for the maintenance and replacement of the acoustic emitter 27 and the receiving plate 28. (4) The motor, the acoustic emission assembly, the acoustic reception assembly, and other equipment are connected to the outside through the high-pressure-resistant pipeline component 31, and a low-temperature fluid is injected between the inner pipeline 311 and the outer pipeline 312 to isolate the high-temperature and high-pressure environment inside the cylinder 2, so that the signal line and wire are not easy to be damaged, extending the service life of the cables, and enhancing the safety of the device.

In some embodiments, a return pressure assembly is also included in the displacement device. As shown in FIG. 8, the return pressure assembly may include a return pressure pump 46 and a return pressure pipeline 51. A first end of the return pressure pipeline 51 is connected to the return pressure pump 46, and a second end of the return pressure pipeline 51 is connected to a second discharge port 6. The return pressure 6 51 is provided with a fourth valve 48 and a return pressure medium container 47 at an end near the return pressure pump 46. A return pressure medium is injected from the return pressure medium container 47 into the interior of the cylinder 2 from the second discharge port 6 through a cooperation between the return pressure pump 46 and the fourth valve 48.

The return pressure assembly refers to an assembly that applies pressure to the interior of the cylinder 2 through the second discharge port 6. In some embodiments, the return pressure assembly may be disposed outside the cylinder 2.

The return pressure medium container 47 refers to a container for storing a return pressure medium. The return pressure medium is a gas intended to be input into the rock plate 16 to elevate the internal pressure of the rock plate 16. In some embodiments, the return pressure medium may be an inert gas, such as nitrogen, etc.

In some embodiments, the return pressure medium may be conveyed through a return pressure pipeline to the second discharge port 6 to be injected into the rock plate 16 via the discharge pipeline 15.

In some embodiments, the return pressure pump 46 may be a peristaltic pump or a centrifugal pump, etc.

In some embodiments, in establishing the pressure conditions of the original formation, the confining pressure (i.e., the external pressure) of the plate model 45 may be provided by the confining pressure pump 43, and the internal pressure of the flatbed model 45 may be provided simultaneously by the return pressure pump 46 and the displacement pump 37. When the displacement pump 37 is operating to pressurize the plate model 45, the third valve 56 of the gaseous medium container 40 needs to be opened to inject gas into the plate model 45. Due to the sealing performance of the cylinder 2 and the plate model 45, the liquids and/or gases in the plate model 45 may be discharged from the discharge pipeline 15. At this time, the return pressure pump 46 works, the fourth valve 48 is opened, and the return pressure medium is injected into the plate model 45 to increase the internal pressure of the plate model 45 to balance the internal and external pressure of the plate model 45.

In some embodiments, the valves corresponding to the plurality of displacement medium containers may also be closed when the pressure conditions of the original formation are established, with the displacement pump 37 inoperative, and the internal pressure of the plate model 45 is provided by the displacement pump 46 alone. However, in the subsequent experiments, the displacement pump 37 may be firstly started, the outlet pressure of the displacement medium container is raised, equalizing the pressures on two sides of the valves of the displacement medium container, and then opening the corresponding valves of the displacement medium container to prevent the internal pressure in the plate model 45 from being too high and impacting the displacement medium container.

More descriptions regarding establishing the pressure conditions in the original formation may be found in related descriptions hereinafter.

Some embodiments of the present disclosure also provide a forklift 8. When the plate model 45 needs to be mounted, an extension arm of the forklift 8 may be connected to the first cover plate 101, and the rest of the forklift 8 is the same as a conventional forklift 8, including a lift frame, a brake handle 11, a lift handle 12, or the like.

In some embodiments, the forklift 8 is connected to the first cover plate 101 with a freely rotatable bearing 10, which is electrically connected to the second motor 91. The second motor 91 may drive the bearing 10 to rotate, which in turn rotates the rock plate 16 that is connected to the first cover plate 101.

In some embodiments, the output shaft of the second motor 91 may be connected to the bearing 10. When the second motor 91 is rotated, the output shaft of the second motor 91 drives the bearing 10 to rotate, thereby driving the first cover plate 101 to rotate, which in turn drives the plate model 45 connected to the first cover plate 101 to rotate.

Separating and installing the first cover plate 101 and the cylinder 2 through the forklift 8 and operating the lift handle 12 and the brake handle 11 of the forklift 8 facilitate the removal or loading back of the plate model 45 from the cylinder 2.

In some embodiments, conducting the displacement experiment utilizing the displacement device described in the preceding embodiments may include the following operations.

In S100, the plate model 45 may be manufactured.

A sand filling scheme may be determined based on relevant core data provided at an oilfield site, and a small piece of plunger core may be taken from the fabricated sand filling model to determine the permeability, porosity, and other physical parameters of the rock. If the parameters satisfy experimental requirements, the fabricated sand filling model may be filled into the model cavity 17 as the rock plate 16 after drying and curing. The model cavity 17 is then sealed using a sealing member. Further, the second injection port 5 of the plate model 45 may be connected to the third injection port of the first cover plate 101, and the second discharge port 6 of the plate model 45 may be connected to the third discharge port of the first cover plate 101.

After manufacturing the plate model 45, the outstretched arm of the forklift 8 may be utilized to dock with the bearing 10 on an outer side of the first cover plate 101 and drive the bearing 10 to rotate through the first motor 55, which in turn drives the first cover plate 101 to rotate. The plate model 45 may be driven to rotate because the plate model 45 is fixedly connected to the first cover plate 101. In some embodiments, the forklift 8 may rotate the plate model 45 into the cylinder 2 and rotate the plate model 45 to a vertical state (i.e., so that the plane of the rock plate 16 is perpendicular to the ground plane). After the plate model 45 is placed, the first cover plate 101 is sealed and fastened to the cylinder 2 by the bolt 33 and the sealing rubber ring.

In S200, the sealing performance of the displacement device may be tested.

One end of the pressurized pipeline 36 is connected to the first injection port 4, the fluid in the pressurized pipeline 36 is pressurized by the pressurized pump 32, so that the fluid is injected into the interior of the cylinder 2 from the first injection port 4, and the air in the cylinder 2 is discharged from the first discharge port 7. After the air in the interior of the cylinder 2 is completely discharged, the first discharge port 7 is connected to the other end of the pressurized pipeline 36. Then the confining pressure inside the cylinder 2 is increased to 5 MPa by the confining pressure pump 43, and then it is left to stand for 24 hours. If data of a pressure gauge 42 does not change, the sealing performance is indicated to be good, and if the data of the pressure gauge 42 decreases, then the displacement device is indicated to have a leakage problem and the sealing performance is poor.

In S300, the temperature and pressure conditions of the original formation may be established.

One end of the pressurized pipeline 36 is kept connected to the first injection port 4 and the other end of the pressurized pipeline 36 is connected to the first discharge port 7. The internal pressure of the plate model 45 (i.e., the internal pressure of the rock plate 16) is gradually increased by the displacement pump 37, while the return pressure inside the cylinder 2 is continuously boosted by the return pressure pump 46, increasing the return pressure (which is a pressure applied to the cylinder 2 by the return pressure pump 46) inside the cylinder 2. The confining pressure outside the plate model 45 is always kept at a level that is 5 MPa higher than the inlet pressure of the displacement pump 37 (i.e., the pressure of the first discharge port 7) to maintain the sealing performance of the plate model 45. By continuously increasing the internal pressure of the plate model 45 by the displacement pump 37, ultimately, the internal pressure of the plate model 45 rises to the formation pressure and stays constant.

In addition, during the boosting process of the displacement pump 37, the pressurized pipeline 36 is heated by the heating coil 34, and the fluid at a set temperature in the pressurized pipeline 36 is injected into the interior of the cylinder 2 through the first injection port 4 by the pressurized pump 32, so that the temperature inside the cylinder 2 is maintained at the set temperature.

In such a case, the pressure in the cylinder 2 (the confining pressure of the plate model 45) may be raised to a simulated formation pressure and the temperature is constant at a simulated formation temperature.

In S400, a bound water saturation of rock plate 16 may be established.

The water delivery valve is opened, and the water medium (e.g., the formation water) in a water storage container is injected into the rock plate 16 of the plate model 45 through the second injection port 5 until the formation water flows out of the second discharge port 6, the displacement pump 37 is turned off and the data is recorded. At this point, the plate model 45 is filled with the formation water. The rock plate 16 is scanned using the acoustic detection component to ensure that the formation water is evenly distributed in each region of the rock plate 16. If the acoustic detection component detects that the formation water is not uniformly distributed in the rock plate 16, the displacement pump 37 is controlled to continue injecting formation water into the rock plate 16 until the formation water is uniformly distributed in the rock plate 16. Subsequently, the second valve 58 of the water storage container is closed, the fourth valve 48 is opened, the return pressure pump 46 is driven, the return pressure medium (e.g., nitrogen) is fed into the rock plate 16 from the second injection port 5, and the formation water in the rock plate 16 is discharged out of the second discharge port 6. Then, the bound water saturation is built up until there is no water coming out of the second discharge port 6, and the total amount of water discharged is recorded.

In S500, an analog oil may be input.

The analog oil in an oil storage container is injected into the rock plate 16 from the second injection port 5 via the displacement pump 37 until the analog oil overflows from the second discharge port 6. The rock plate 16 is scanned using the acoustic detection component. When the scanning results of the acoustic detection component show that the analog oil is evenly distributed, the displacement pump 37 stops working, and an outflow volume and an inlet pumping volume are recorded.

The outflow volume refers to an amount of the analog oil overflowing from the second discharge port 6, and the inlet pumping volume refers to an amount of the analog oil pumped out of the oil storage container. The total amount of the analog oil in the plate model 45 may be obtained by subtracting the two.

In S600, experiments of oil displacement by water/gas may be performed.

The experiments of oil displacement by water/gas are performed at formation temperature and pressure by injecting the gaseous medium in a gaseous storage container or the water medium (e.g., formation water) in the water storage medium into the rock plate 16 through the second injection port 5 by the displacement pump 37 at a constant speed to displace the analog oil from the rock plate 16 through the second discharge port 6. For every 0.02 HCPV of the gaseous medium or the water medium injected, a pressure, an amount of water injected, and an amount of oil and water discharged from the second injection port 5 and the second discharge port 6 are recorded. At the same time, the acoustic detection component is utilized to scan the whole rock plate 16 to obtain acoustic wave time lag variation at various locations on the rock plate 16. When the second discharge port 6 does not produce oil and begins to produce gas or water continuously, the experiment is stopped and the data is recorded.

The amount of water injected is the amount of water medium pumped out of the water storage container. The amount of oil and water discharged refers to an amount of water and an amount of oil that are discharged from the second discharge port 6.

In S700, experimental data may be processed.

The data is transmitted to a terminal through the signal line. Then, the data is organized, calculated, and analyzed to obtain data such as oil-water displacement efficiency or the oil-gas displacement efficiency and the analog oil recovery rate, etc.

In some embodiments, a processor 49 and a controller (not shown in the accompanying drawings) are provided in the displacement device. The processor 49 is configured on a terminal device, and the processor 49 is communicatively connected to the controller through communication lines. The controller is communicatively connected to the confining pressure pump, the displacement pump, and the acoustic detection component, and the controller is communicatively connected to a control assembly of a plurality of valves. The controller is communicatively connected to a plurality of components and may control the corresponding components to realize their functions. For example, the controller may control the acoustic detection component to initiate scanning, and control the first valve, the second valve, etc., to be opened or closed.

In some embodiments, gas flowmeters 54 and discharge valves 41 are provided at the first discharge port and the second discharge port. The gas flowmeters 54 are communicatively connected to the processor 49 through communication lines, and the controller is communicatively connected to the control assembly of the discharge valves 41. The gas flow meter 54 may be configured to detect whether gas is discharged from the first discharge port or the second discharge port.

In some embodiments, the processor 49 is configured to issue a confining pressure control command to the controller in response to the gas flow meter 54 detecting that there is no gas discharge. The controller is configured to control the discharge valve 41 to close in response to receiving the confining pressure control command and control the confining pressure pump to perform pressurization on the cylinder.

The confining-pressure control command is used to control the controller to carry out commands for applying the confining pressure to the rock plate.

In some embodiments, the controller may control the discharge valve 41 to close in response to receiving the confining-pressure control command to detect the sealing performance of the displacement device. More descriptions regarding testing the sealing performance of the displacement device may be found in the related descriptions hereinabove.

In some embodiments, the controller may control the confining pump to perform the pressurization on the cylinder in response to a test result indicating that the sealing performance is good. In some embodiments, while the confining pump is performing the pressurization on the cylinder, the controller may also control the displacement pump to increase the internal pressure of the plate model, and control a heater in the circulation component to heat the pressurization pipeline 36 to allow the fluid in the pressurized pipeline 36 reaches a set temperature, which in turn allows the confining pump to inject fluid at the set temperature into the interior of the cylinder. The temperature inside the cylinder is maintained at the set temperature while the confining pressure pump performs the pressurization on the cylinder.

In some embodiments, the pressurized pipeline is provided with a flowrate regulating assembly 53, and a plurality of temperature-sensitive elements 35 are provided inside the cylinder 2 and the pressurized pipeline. The temperature-sensitive elements 35 are communicatively connected to the processor 49 through communication lines, and the flowrate regulating assembly 53 is communicatively connected to the controller.

In some embodiments, the processor 49 is configured to issue a regulation command to the controller in response to determining that a difference in temperature data at a plurality of preset locations satisfies a temperature difference threshold. The controller is configured to, in response to receiving the regulating command, control the confining pressure pump and/or the flowrate regulating assembly 53 to regulate a circular flow cycle of the fluid in the pressurized pipeline 36.

The preset location refers to a location set for temperature monitoring within the cylinder. For example, the plurality of preset locations may be a plurality of locations at which the temperature-sensitive elements 35 are set, etc.

The regulation command refers to a command for regulating the circular flow cycle. For example, to increase or decrease the circular flow cycle. In some embodiments, when the difference in the temperature data at the plurality of preset locations exceeds the temperature difference threshold, it indicates that the temperature of the fluid inside the cylinder is not uniformly distributed. At this time, the processor 49 may send the regulation command to the controller to regulate the circular flow cycle.

In some embodiments, the processor 49 may calculate a difference in temperature data (i.e., a temperature difference) between any two of the plurality of preset locations. In response to a preset count of temperature differences exceeding the temperature difference threshold, the regulation command is issued to the controller.

In some embodiments, the processor 49 may also calculate a standard deviation or variance of the temperature data for the plurality of preset locations. In response to the standard deviation or variance exceeding a corresponding temperature difference threshold, the regulation command is issued to the controller.

The flowrate regulating assembly 53 refers to a component for regulating the flowrate of the fluid in the pressurized pipeline 36. For example, the flowrate regulating assembly 53 may be a flowrate regulating valve, etc.

The circular flow cycle refers to the time taken for the fluid to flow along the pressurized pipeline 36 of the circulation component and the annular pathway formed in the cylinder for one round. The faster the fluid flow rate, the shorter the circular flow cycle. The circular flow cycle may be regulated by regulating the fluid flow rate.

In some embodiments, the controller may, in response to receiving the regulation command, control the power of the confining pump and/or control the size of the valve of the flowrate regulating valve to regulate the fluid flow rate, thus regulating the circular flow cycle.

In some embodiments, the circular flow cycle may be divided into a plurality of levels, such as a cycle every 30 s, a cycle every 50 s, a cycle every 70 s, or the like. In some embodiments, the controller may regulate the circular flow cycle into other levels in response to receiving the regulation command.

In some embodiments, the processor 49 may, in response to adjustments made to the circular flow cycle reaching a preset count, stop issuing the regulation command to the controller and control an alarm device to emit an alarm.

In some embodiments, the processor 49 may also be configured to determine an updated circular flow cycle based on distances and temperature differences between the plurality of preset locations, and a pressure stabilization degree.

The distances between the plurality of preset locations may include a distance between any two of the plurality of preset locations. The distances between the plurality of preset locations may be input into the processor 49 in advance.

In some embodiments, the processor 49 may calculate an average distance based on the distances between the plurality of preset locations, and calculate, by a preset algorithm, to determine the updated circular flow cycle based on the average distance, a maximum distance between the plurality of preset locations where the temperature difference exceeds the temperature difference threshold, and the pressure stabilization degree.

In some embodiments, the preset algorithm is shown in equation (1) below:

$$T = \frac{d}{r_{max} \times e^{\frac{w}{2}}} \qquad (1)$$

T denotes the updated circular flow cycle, d denotes the average distance, $r_{max}$ denotes the maximum distance between a plurality of preset locations where the temperature difference exceeds the temperature difference threshold, and w denotes the pressure stabilization degree.

The average distance refers to the average distance between every two neighboring temperature-sensitive elements 35 (or preset locations).

The maximum distance between the plurality of preset locations where the temperature difference exceeds the temperature difference threshold may reflect the temperature distribution of the fluid within the cylinder 2 on a larger scale. If the temperature difference between neighboring temperature-sensitive elements 35 is too large, it may be an accidental situation or external interference rather than a problem with the circulation heating. Thus, using the maximum distance between the plurality of preset locations that exceed the temperature difference threshold as a judgment criterion may more truly reflect the temperature distribution of the fluid in the cylinder, and thus more accurately determine the updated circular flow cycle. Then the updated circular flow cycle may be effectively and automatically regulated, which saves labor and material resources and meets the experimental requirements.

The pressure stabilization degree refers to a stabilization degree of the confining pressure inside the cylinder when the simulated formation pressure is reached. The pressure stabilization degree may reflect the fluctuation of pressure inside the cylinder. The more violent the fluctuation of the confining pressure inside the cylinder, the lower the pressure stabilization degree. Because the pressure stabilization degree relates to the safety of the pressure inside the cylinder, the lower the pressure stabilization degree, the smaller the adjustment of the circular flow cycle.

The pressure stabilization degree may be determined in a plurality of ways. In some embodiments, the pressure stabilization degree may be obtained by dividing a difference between an upper fluctuation limit and a lower fluctuation limit by a fluctuation reference value.

The upper fluctuation limit refers to the maximum value of the pressure in the cylinder during a preset time period. The lower fluctuation limit refers to the minimum value of the pressure in the cylinder during the preset time period. The fluctuation reference value refers to a reference value when the pressure in the cylinder fluctuates.

The fluctuation reference value may be determined in a plurality of ways. For example, the processor 49 may determine fluctuation reference value by querying a table of preset reference values based on different pressures (the maximum pressure value is theoretically the simulated formation pressure) in the pressurization process.

In some embodiments, the table of preset reference values includes correspondences between different pressure values and different fluctuation reference values. For example, a pressure at 11 MPa corresponds to a fluctuation reference value of 11 MPa. In some embodiments, the processor 49 may determine the fluctuation reference value by querying the table of preset reference values based on a current pressure during pressure regulation.

The table of preset reference values may be constructed based on a plurality of ways. For example, the table of preset reference values may be constructed based on historical data, experimental results, or simulations and predictions, etc. For example, the table of preset reference values may be constructed based on historical adjustments, with fluctuating reference values for a plurality of scenarios where the pressure stabilization degree is more accurately calculated being the fluctuating reference value for the scenario.

More descriptions regarding the pressure stabilization degree may be found in the related descriptions hereinafter.

In some embodiments, in response to the circular flow cycle being updated, the processor 49 may issue the regulation command to the controller to cause the controller to adjust a heating power of the heating coil.

A target value of the heating power may be determined in a plurality of ways. The target value of the heating power refers to an adjusted heating power. In some embodiments, the processor 49 may determine, based on the temperature data at different preset locations, a temperature of the fluid in the first injection port, and a temperature of the fluid in the first discharge port, by matching through a vector database, the heating power target value.

In some embodiments, the processor 49 may construct vectors to be matched based on the temperature data at different preset locations, the temperature of the fluid in the first injection port, and the temperature of the fluid in the first discharge port. The processor 49 may also determine one or more target vectors whose matching similarity is higher than a similarity threshold by matching the vectors to be matched in the vector database. The processor 49 may further obtain the target value of the heating power corresponding to the vectors to be matched based on reference heating powers corresponding to one or more target vectors.

In some embodiments, the vector database includes a plurality of reference vectors, and a reference heating power corresponding to each reference vector. The reference vectors are constructed based on historical temperature data at different preset locations during various historical regulation processes, a historical temperature of the fluid in the first injection port, and a historical temperature of the fluid in the first discharge port, with each reference vector corresponding to a reference heating power.

In some embodiments, the vector database may be constructed by a remote server and pre-stored in processor 49.

Due to problems with the circulation heating system and the influence of the external environment, the temperatures at different locations of the cylinder may be inconsistent or deviate excessively from the preset temperature. By monitoring the temperature difference between different locations of the cylinder, considering the distance between different monitoring locations of the cylinder being too small, it is possible to effectively and automatically control the circular flow cycle, which saves manpower and material resources while meeting the experimental requirements. In addition, in response to the circular flow cycle being updated, the heating power is determined by matching the vector database constructed from historical data, enabling the power of the circular heating system to be adjusted in an informed manner to avoid heating that does not meet the temperature requirements.

In some embodiments, a pressure sensor 52 is provided on the inner wall of the cylinder and a cover plate (e.g., the first cover plate and/or the second cover plate), and the pressure sensor 52 is communicatively connected to the processor 49 through communication lines.

In some embodiments, the processor 49 is configured to determine the pressure stabilization degree based on a pressure sequence acquired by pressure sensor 52. In response to the pressure stabilization degree being higher than a pressure stabilization threshold, the processor 49 issues a pressure stabilization simulation command to the controller.

The pressure sequence refers to a sequence including a plurality of pressure data. The pressure sequence includes pressure data from at least one acquisition time point. The at least one acquisition time point refers to a consecutive time point.

When the pressure stabilization degree is higher than the pressure stabilization threshold, and there is a large fluctuation in the pressure inside the cylinder, the processor 49 may send the pressure stabilization simulation command to the controller to enable the controller to perform the corresponding function.

In some embodiments, to determine the pressure stabilization degree, the processor 49 is configured to determine, based on the pressure sequence, an acquisition frequency of the pressure sensors 52 at the at least one acquisition time point; determine pressure fluctuation data based on pressure data at different acquisition frequencies; and determine the pressure stabilization degree based on the pressure fluctuation data.

In some embodiments, the acquisition frequency may be determined in a plurality of ways. For example, the processor 49 may determine the acquisition frequency by querying a table of preset acquisition frequencies based on different pressure intervals during a pressure rising process.

In some embodiments, the table of preset acquisition frequencies may include different pressure intervals in the pressure rising process and corresponding acquisition frequencies. For example, when the pressure interval is from 5 Mpa to 10 MPa, the corresponding acquisition frequency is 10 times/min. In some embodiments, the processor 49 may determine the acquisition frequency by querying the table of preset acquisition frequencies based on the pressure interval in which a pressure in the current pressure rising process is located.

The table of preset acquisition frequencies may be constructed based on a plurality of ways. For example, the table of preset acquisition frequencies may be constructed based on historical data, experimental results, or simulations and predictions, etc. For example, the table of preset acquisition frequencies may be constructed based on historical pressure conditions, with a collection frequency with which data acquired at various pressure intervals more closely reflects the actual pressure being the collection frequency for that pressure interval.

The pressure fluctuation data refers to a deviation value of the pressure value of the pressure sensor 52 that is monitored to deviate from a theoretical pressure value at the acquisition time point corresponding to the acquisition frequency. In some embodiments, the pressure fluctuation data may be positive, negative, and zero, e.g., the pressure fluctuation data may be +50 kPa, −30 kPa, or 0. In some embodiments, the pressure fluctuation data may be serial data. The pressure fluctuation data includes deviation values at different acquisition time points corresponding to different acquisition frequencies.

In some embodiments, the processor 49 may determine the pressure stabilization degree based on the pressure fluctuation data in a plurality of ways. For example, the processor 49 may designate a ratio of a sum of the deviation values of the plurality of acquisition time points to a count of the acquisition time point as the pressure stabilization degree. The count of acquisition time points is equal to the count of types of acquisition frequencies.

In some embodiments, the processor 49 may calculate, based on the pressure fluctuation data, a local pressure fluctuation amplitude and a global pressure fluctuation amplitude for a preset time period based on the pressure fluctuation data; and determine the pressure stabilization degree by a weighted fusion based on the local pressure fluctuation amplitude, the global pressure fluctuation amplitude, and a count of fluctuations.

The preset time period refers to a time period corresponding to different pressure intervals during the pressure rising process. More descriptions regarding the pressure intervals may be found in related descriptions hereinabove.

The local pressure fluctuation amplitude refers to a pressure fluctuation amplitude during a part of the preset time period. The global pressure fluctuation amplitude refers to a pressure fluctuation amplitude during the whole preset time period.

In some embodiments, the processor 49 may divide the preset time period into a plurality of sub-time periods, determine a difference between a maximum deviation value and a minimum deviation value at each sub-time period based on the pressure fluctuation data, and designate the difference as the local pressure fluctuation amplitude at each sub-time period.

In some embodiments, the processor 49 may determine the difference between the maximum deviation value and the minimum deviation value for a preset time period based on the pressure fluctuation data and designate the difference as the global pressure fluctuation amplitude for the preset time period. For example, the preset time period is uniformly divided into five sub-time periods, the difference between the maximum deviation value and minimum deviation value at each sub-time period is the local pressure fluctuation amplitude, and the maximum deviation value and minimum deviation value at the whole preset time period are the global pressure fluctuation amplitude.

A count of fluctuations refers to a count time points at which pressure fluctuations occur. For example, a count of acquisition time points in which a deviation value exists within the preset time period is determined as the count of fluctuations.

In some embodiments, the pressure stabilization degree is determined by weighted fusion using the following equation (2):

$$P_s = e^{\left(-\left[P_A \times W_A - \sum_{i=1}^{N}(P_i \times W_i)\right]\right)} \tag{2}$$

$P_s$ denotes the pressure stabilization degree, $P_A$ denotes the global pressure fluctuation amplitude, $W_A$ denotes a weight corresponding to the global pressure fluctuation amplitude, $P_i$ denotes the local pressure fluctuation amplitude at the i-th sub-time period, $W_i$ denotes a weight corresponding to the local pressure fluctuation amplitude at the ith sub-time period, e denotes the exponential function, and N denotes the count of sub-time periods included in the preset time period.

Understandably, due to changes in the operational stability of the confining pump (caused by fluctuations in current and voltage), the influence of external factors, etc., the pressure during the pressure rising process does not always present as the theoretical pressure, but rather there are different degrees of deviation from the theoretical pressure. As a result, by adjusting the acquisition frequency at different confining pressure pressures, more reliable pressure fluctuation data may be monitored. Some embodiments of the present disclosure determine the pressure fluctuation data based on the pressure data under different acquisition frequencies, thus determining the pressure stabilization degree, which may reasonably and automatically assess whether the device meets the preset experimental conditions and ensure experimental quality and accuracy. On the other hand, the acquisition frequency is not only related to the pressure during the pressurization process, but also the pressure fluctuation. Some embodiments of the present disclosure may ensure the reliability of the pressure monitoring by detecting the pressure fluctuation to avoid problems of useless monitoring and inadequate monitoring. Additionally, by considering local pressure fluctuations and global pressure fluctuations, and then determining the pressure stabilization degree, the assessment of the results of the pressure stabilization degree by individual pressure fluctuations caused by accidental disturbing factors is effectively avoided, and the reliability of the pressure monitoring is improved.

In some embodiments, the processor 49 is further configured to determine an optimized acquisition frequency by processing the pressure data at the different acquisition frequencies and the pressure fluctuation data based on an acquisition frequency evaluation model; and update the acquisition frequency of the pressure sensors 52 based on the optimized acquisition frequency.

The acquisition frequency evaluation model may be a machine learning model. In some embodiments, the acquisition frequency evaluation model may be any one or a combination of a plurality of feasible models such as a deep neural network (DNN) model, a convolutional neural network (CNN) model, or the like. In some embodiments, an inputs of the acquisition frequency evaluation model may include pressure data, pressure fluctuation data, and a preset acquisition frequency at different acquisition frequencies, and an output of the acquisition frequency evaluation model may be a coverage of the preset acquisition frequency.

In some embodiments, the processor 49 may designate the acquisition frequency determined based on the table of preset acquisition frequencies as the preset acquisition frequency.

The coverage refers to a parameter used to assess whether the acquisition frequency is capable of capturing pressure fluctuations. For example, in an extreme case, if the pressure data is collected only for the two time points at two ends of the preset time period, pressure fluctuations in the time period are not captured, and the coverage is low at this time, and it is not possible to effectively capture the pressure fluctuations.

In some embodiments, the acquisition frequency evaluation model may be obtained by training in a plurality of manners based on a plurality of labeled training samples with labels. For example, the training may be performed based on supervised learning. Merely by way of example, a plurality of training samples with labels may be input into an initial acquisition frequency evaluation model to obtain the coverage. A loss function may be constructed from the labels and the output results of the initial acquisition frequency evaluation model, and the parameters of the initial acquisition frequency evaluation model are iteratively updated based on the loss function. When the loss function of the initial acquisition frequency evaluation model meets a preset condition, the model training is completed and a trained acquisition frequency evaluation model is obtained. The preset condition may be that the loss function converges, a count of iterations reaches a threshold, etc.

In some embodiments, the training samples may include sample pressure data at a plurality of sample acquisition frequencies, sample pressure fluctuation data, and a sample preset acquisition frequency. The label may be a coverage at the sample preset acquisition frequency.

In some embodiments, the training samples and the corresponding labels may be determined based on historical data. For example, the coverage corresponding to different historical acquisition frequencies is evaluated based on historical trial data and results. If all deviation values may be detected for a historical acquisition frequency, the label corresponding to the historical acquisition frequency (i.e., the coverage of the historical acquisition frequency) is labeled as 1. If a deviation value from a predetermined quantity threshold cannot be detected for a certain historical acquisition frequency, the label corresponding to the historical acquisition frequency is labeled as 0. If a count of the detected deviation values for a particular history acquisition frequency is greater than a preset count threshold but not all of them are detected, the label corresponding to the history acquisition frequency is labeled with a value from 0 to 1. The preset count threshold may be a system preset value, a human preset value, etc.

In some embodiments, the processor 49 may not update the acquisition frequencies of the pressure sensors 52 in response to the preset acquisition frequencies having a coverage greater than a coverage threshold.

In some embodiments, the processor 49 may determine an optimized acquisition frequency in response to the coverage of the preset acquisition frequency not being greater than the coverage threshold, and update the acquisition frequency of the pressure sensor 52 to the optimized acquisition frequency.

In some embodiments, the processor 49 may determine an optimized acquisition frequency in a plurality of ways. For example, processor 49 may increase the acquisition frequency based on a preset ratio.

In some embodiments of the present disclosure, determining whether or not to update the acquisition frequency of the pressure sensor 52 based on the coverage of the preset acquisition frequency may avoid insufficient acquisition and over acquisition.

In some embodiments, the controller is communicatively connected to the control assembly of the second valve and the fourth valve and communicatively connected to the acoustic detection component.

In some embodiments, the controller may, in response to receiving the pressure stabilization simulation command, control the second valve to open and control the displacement pump to inject the water medium in the water medium container into the plate model; control the acoustic detection component to perform a scanning operation on the plate model to obtain first scanning information, and send the first scanning information to the processor 49 for processing.

In some embodiments, the processor 49 may determine, based on the first scanning information, a first distribution uniformity of the water medium injected into the plate model; and in response to the first distribution uniformity satisfying a first distribution condition, issues a first control command to the controller to cause the controller to control the second valve to close and control the fourth valve to open.

The first scanning information refers to scanning data reflecting the distribution of stratum water in the plate model. In some embodiments, the first scanning information may be matrix data, with elements in the matrix reflecting scanning data at different location coordinates of the plate model.

The first distribution uniformity refers to a distribution uniformity of the water medium in the plate model.

In some embodiments, the processor 49 may determine, based on elements in the first scanning information (i.e., elements in the matrix), a difference value between the scanning data and preset baseline data at different locations in the plate model; determine that the water medium is unevenly distributed (e.g., is not filled or has air bubbles) at the location when the difference value exceeds a difference threshold; and count a ratio of a count of locations where all the difference values exceed the difference threshold to a total count of locations as the uniformity of the distribution of the water medium in the plate model.

In some embodiments, the first distribution condition may be that the first distribution uniformity is greater than a first uniformity threshold. When the first distribution uniformity satisfies the first distribution condition, a first control command may be issued to the controller to cause the controller to control the second valve to close and control the fourth valve to open. In some embodiments, the controller may further control the return pressure pump to inject the pressure medium into the plate model. The first uniformity threshold may be a system default value, an empirical value, a human preset value, etc., or any combination thereof, and may be set according to actual needs.

When the gas flowmeter 54 detects that there is no gas being discharged, the water medium may be displaced using the displacement pump and the bound water saturation may be established using the return pressure pump.

In some embodiments, the controller is communicatively connected to a control component of the first valve, the second valve, and the third valve, as well as communicatively connected to the acoustic detection component.

In some embodiments, the controller may, in response to the gas flowmeter 54 detecting that no gas is being discharged, control the third valve to open and control the displacement pump to inject the oil medium from the oil medium container into the plate model; obtain second scanning information by controlling the acoustic detection component to perform a scanning operation on the rock plate of the plate model and send the second scanning information to the processor 49 for processing.

In some embodiments, the processor 49 may determine, based on the second scanning information, a second distribution uniformity of the oil medium injected into the plate model; and in response to the second distribution uniformity satisfying a second distribution condition, issues a second control command to the controller.

In some embodiments, the controller may, in response to receiving the second control command, control the first valve or the second valve to open, and control the displacement pump to inject the water medium in the water medium container or the gaseous medium in the gaseous medium container into the plate model, to obtain oil displacement data; and control the acoustic detection component to perform the scanning operation on the rock plate of the plate model to obtain acoustic wave time lag variation data.

The second scanning information refers to scanning data reflecting the distribution of the oil medium in the plate model. In some embodiments, the second scanning information may also be matrix data, where the elements in the matrix may reflect scanning data at different location coordinates of the plate model.

The second distribution uniformity refers to the distribution uniformity of the medium in the plate model. The second distribution uniformity is determined like the determination of the first distribution uniformity, and may not be repeated herein.

In some embodiments, the second distribution condition may be that the second distribution uniformity is greater than a second uniformity threshold. When the second distribution uniformity satisfies the second distribution condition, a second control command may be issued to the controller to cause the controller to control the first valve or the second valve to open. The second uniformity threshold may be a system default value, an empirical value, a human preset value, etc., or any combination thereof, and may be set according to the actual needs.

The oil displacement data refers to data related to the displacement simulation oil in the displacement experiment, such as one or more of a second injection port pressure, a second discharge port pressure, an injection volume or a gas injection volume, an oil discharge volume, a water discharge volume, or the like.

When the gas flowmeter 54 detects that no gas is discharged, the oil medium may be input into the plate model first by using the displacement pump, and then the oil medium in the plate model may be displaced by using the water medium or the gaseous medium to complete the displacement experiment.

In some embodiments, the displacement device further comprises a display screen. The display screen is configured to display a monitoring parameter and detect the monitoring parameter including at least one of flow rate data, temperature data, and pressure data. Displaying the monitoring parameter through the display screen helps the experimenter observe the experimental process.

Having thus described the basic concepts, it may be rather apparent to those skilled in the art after reading this detailed disclosure that the foregoing detailed disclosure is intended to be presented by way of example only and is not limiting. Although not explicitly stated here, those skilled in the art may make various modifications, improvements, and amendments to the present disclosure. These alterations, improvements, and amendments are intended to be suggested by this disclosure and are within the spirit and scope of the exemplary embodiments of the present disclosure.

Moreover, certain terminology has been used to describe embodiments of the present disclosure. For example, the terms "one embodiment," "an embodiment," and/or "some embodiments" mean that a particular feature, structure, or feature described in connection with the embodiment is included in at least one embodiment of the present disclosure. Therefore, it is emphasized and should be appreciated that two or more references to "an embodiment" or "one embodiment" or "an alternative embodiment" in various portions of the present disclosure are not necessarily all referring to the same embodiment. In addition, some features, structures, or characteristics of one or more embodiments in the present disclosure may be properly combined.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. However, this disclosure does not mean that object of the present disclosure requires more features than the features mentioned in the claims. Rather, claimed subject matter may lie in less than all features of a single foregoing disclosed embodiment.

In some embodiments, the numbers expressing quantities or properties used to describe and claim certain embodiments of the present disclosure are to be understood as being modified in some instances by the term "about," "approximate," or "substantially." For example, "about," "approximate" or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable.

Each of the patents, patent applications, publications of patent applications, and other material, such as articles, books, specifications, publications, documents, things, and/ or the like, referenced herein is hereby incorporated herein by this reference in its entirety for all purposes. History application documents that are inconsistent or conflictive with the contents of the present disclosure are excluded, as well as documents (currently or subsequently appended to the present specification) limiting the broadest scope of the claims of the present disclosure. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the present disclosure disclosed herein are illustrative of the principles of the embodiments of the present disclosure. Other modifications that may be employed may be within the scope of the present disclosure. Thus, by way of example, but not of limitation, alternative configurations of the embodiments of the present disclosure may be utilized in accordance with the teachings herein. Accordingly, embodiments of the present disclosure are not limited to that precisely as shown and described.

What is claimed is:

1. A displacement device, comprising:
a plate model including a model cavity and a rock plate disposed within the model cavity, wherein:
a sealing member is provided on an outer surface of the model cavity, at least one electrode sheet is embedded in the sealing member, and the rock plate is sealed by the sealing member and the model cavity; and
an injection pipeline and a discharge pipeline are inserted at opposite ends of the rock plate, respectively;
a cylinder provided with cover plates at two ends along an axial direction, wherein:
a first cover plate in the cover plates is provided with a first injection port, a second injection port, and a second discharge port, a second cover plate in the cover plates is provided with a first discharge port, and the first injection port and the first discharge port are connected to an interior of the cylinder;
the second injection port is connected to the injection pipeline, and the second discharge port is connected to the discharge pipeline;
a circulation component including a pressurized pump and a pressurized pipeline, wherein:
a first end of the pressurized pipeline is connected to the first injection port, a second end of the pressurized pipeline is connected to the first discharge port, the pressurized pipeline is connected to the pressurized pump at a location close to the second end of the pressurized pipeline by a pipeline branch, and the pressurized pump pressurizes a fluid in the pressurized pipeline;
a confining pressure pump, wherein the confining pressure pump is connected to the second end of the pressurized pipeline; and the confining pressure pump drives a pressurized fluid inside the pressurized pipeline to be injected into the interior of the cylinder from the first injection port to exert a confining pressure on the plate model;
a displacement component including a displacement pump and at least one displacement medium container, wherein the at least one displacement medium container is connected to the second injection port through a displacement pipeline;
and the displacement pump drives a displacement medium inside the at least one displacement medium container to be injected into the rock plate from the second injection port;
an acoustic detection component including an acoustic emission assembly and an acoustic reception assembly, wherein the acoustic emission assembly and the acoustic reception assembly are disposed in parallel on both sides of the plate model, and an acoustic signal generated by the acoustic emission assembly passes through the rock plate through the at least one electrode sheet and is received by the acoustic reception assembly; and
a pipeline component including an inner pipeline and an outer pipeline sleeved over the inner pipeline, wherein a fluid is provided between the outer pipeline and the inner pipeline, and the inner pipeline is internally configured to thread cables.

2. The displacement device of claim 1, wherein the at least one displacement medium container includes a gaseous medium container, a water medium container, and an oil medium container, and the displacement pipeline is provided with a first valve, a second valve, and a third valves; wherein:
a gaseous medium inside the gaseous medium container is injected into the rock plate from the second injection port through a cooperation between the displacement pump and the first valve;
a water medium inside the water medium container is injected into the rock plate from the second injection port through a cooperation between the displacement pump and the second valve; and an oil medium inside the oil medium container is injected into the rock plate from the second injection port through a cooperation between the displacement pump and the third valve.

3. The displacement device of claim 2, wherein the displacement device further comprises a return pressure assembly; wherein:

the return pressure assembly includes a return pressure pump and a return pressure pipeline, a first end of the return pressure pipeline is connected to the return pressure pump, a second end of the return pressure pipeline is connected to the second discharge port, and the return pressure pipeline is provided with a fourth valve and a return pressure medium container at an end near the return pressure pump; and a return pressure medium is injected from the return pressure medium container into the interior of the cylinder from the second discharge port through a cooperation between the return pressure pump and the fourth valve.

4. The displacement device of claim 3, wherein a pressure gauge is provided on the displacement pipeline near the second injection port, a first pressure sensor is provided on the pressurized pipeline near the first discharge port, and/or a second pressure sensor is provided on the return pressure pipeline near the second discharge port.

5. The displacement device of claim 1, wherein the pressurized pipeline is sleeved with a heating coil, and the heating coil heats the fluid inside the pressurized pipeline.

6. The displacement device of claim 1, wherein the sealing member includes a contact layer, a spacer layer, and a pressure-bearing layer, the spacer layer is disposed between the contact layer and the pressure-bearing layer, and the contact layer is disposed in contact with the rock plate.

7. The displacement device of claim 6, wherein a contact area of the spacer layer is smaller than a contact area of the contact layer and a contact area of the pressure-bearing layer, respectively, so that a gap is formed between the contact layer and the pressure-bearing layer.

8. The displacement device of claim 1, wherein the acoustic emission assembly includes an emitter, a guide rail, and a pulley, the emitter is disposed on the pulley, and the pulley is disposed in the guide rail; and the acoustic reception assembly includes a receiver and a receiving plate, the receiver is disposed on the receiving plate, the receiving plate is mounted with rollers, and the rollers are embedded in an inner wall of the cylinder.

9. The displacement device of claim 8, wherein the guide rail is connected to a telescopic rod, and the telescopic rod includes an inner threaded rod and an outer threaded rod, wherein the outer threaded rod is electrically connected to a first motor, and the outer threaded rod is driven to rotate by the first motor to move the acoustic emission assembly.

10. The displacement device of claim 1, wherein the first cover plate is provided with a first support assembly on a side facing the interior of the cylinder, the second cover plate is provided with a second support assembly on a side facing the interior of the cylinder, and the plate model is fixed to the interior of the cylinder by a cooperation between the first support assembly and the second support assembly.

11. The displacement device of claim 1, wherein the first cover plate is detachably connected with the cylinder.

12. The displacement device of claim 1, further comprising a processor and a controller, wherein gas flowmeters and discharge valves are provided at the first discharge port and the second discharge port, the gas flowmeters are communicatively connected to the processor through communication lines, and the controller is communicatively connected to a control assembly of the discharge valves;

the processor, in response to the gas flowmeters detecting that no gas is discharged, issues a confining-pressure control command to the controller; and the controller, in response to receiving the confining-pressure control command, controls the discharge valves to close, and controls the confining pressure pump to perform pressurization on the cylinder.

13. The displacement device of claim 7, further comprising a processor and a controller, wherein the pressurized pipeline is provided with a flowrate regulating assembly, the interior of the cylinder and an interior of the pressurized pipeline are provided with a plurality of temperature-sensitive elements, the temperature-sensitive elements are communicatively connected to the processor through communication lines, and the flowrate regulating assembly is communicatively connected to the controller;

the processor, in response to determining that a difference in temperature data at a plurality of preset locations satisfies a preset condition, issues a regulation command to the controller; and the controller, in response to receiving the regulating command, controls the confining pressure pump and/or the flowrate regulating assembly to regulate a circular flow cycle of a fluid in the pressurized pipeline.

14. The displacement device of claim 1, further comprising a processor and a controller, wherein pressure sensors are provided on an inner wall of the cylinder and the at least one cover plate, and the pressure sensors are communicatively connected to the processor through communication lines;

the processor determines a pressure stabilization degree based on a pressure sequence acquired by the pressure sensors; and in response to the pressure stabilization degree being higher than a pressure stabilization threshold, issues a pressure stabilization simulation command to the controller; wherein the pressure sequence includes pressure data at at least one acquisition time point.

15. The displacement device of claim 14, wherein to determine the pressure stabilization degree based on the pressure sequence acquired by the pressure sensors, the processor is configured to:

determine, based on the pressure sequence, an acquisition frequency of the pressure sensors at the at least one acquisition time point;

determine pressure fluctuation data based on pressure data at different acquisition frequencies; and determine the pressure stabilization degree based on the pressure fluctuation data.

16. The displacement device of claim 15, wherein the processor is configured to:

determine an optimized acquisition frequency by processing the pressure data at the different acquisition frequencies and the pressure fluctuation data based on an acquisition frequency evaluation model; and update the acquisition frequency of the pressure sensors based on the optimized acquisition frequency.

17. The displacement device of claim 15, wherein to determine the pressure stabilization degree based on the pressure fluctuation data, the processor is further configured to:

calculate a local pressure fluctuation amplitude and a global pressure fluctuation amplitude for a preset time period based on the pressure fluctuation data; and determine the pressure stabilization degree by a weighted fusion based on the local pressure fluctuation amplitude, the global pressure fluctuation amplitude, and a count of fluctuations, wherein a weight corresponding to the global pressure fluctuation amplitude is greater than a weight corresponding to the local pressure fluctuation amplitude.

18. The displacement device of claim 14, wherein the controller is communicatively connected to a control assembly of a second valve and a fourth valve and is communicatively connected to the acoustic detection component;

the controller, in response to receiving the pressure stabilization simulation command, controls the second valve to open and controls the displacement pump to inject a water medium from a water medium container into the plate model; and controls the acoustic detection component to perform a scanning operation on the plate model to obtain first scanning information and sends the first scanning information to the processor for processing; and the processor determines, based on the first scanning information, a first distribution uniformity of the water medium injected into the plate model; and in response to the first distribution uniformity satisfying a first distribution condition, issues a first control command to the controller to cause the controller to control the second valve to close and control the fourth valve to open.

19. The displacement device of claim 18, wherein the controller is communicatively connected to a control assembly of a first valve and a third valve;

the controller, in response to determining that gas flowmeters detect no gas discharge, controls the third valve to open and controls the displacement pump to inject an oil medium from an oil medium container into the plate model; controls the acoustic detection component to perform a scanning operation on the plate model to obtain a second scanning information and sends the second scanning information to the processor for processing;

the processor determines, based on the second scanning information, a second distribution uniformity of the oil medium injected into the plate model; and in response to the second distribution uniformity satisfying a second distribution condition, issues a second control command to the controller; and the controller, in response to receiving the second control command, controls the first valve or the second valve to open, and controls the displacement pump to inject the water medium in the water medium container or a gaseous medium in a gaseous medium container into the plate model; and controls the acoustic detection component to perform a scanning operation on the plate model to obtain acoustic wave time lag variation data.

20. The displacement device of claim 1, further comprising a display screen, wherein the display screen is configured to display monitoring parameters, and the monitoring parameters include at least one of flow rate data, temperature data, and pressure data.

* * * * *